US005427785A

United States Patent [19]

Ronson et al.

[11] Patent Number: 5,427,785

[45] Date of Patent: Jun. 27, 1995

[54] RHIZOSHERIC BACTERIA

[75] Inventors: Clive W. Ronson, Concord; Robert W. Kwiatkowski, Randolph, both of Mass.

[73] Assignee: Research Seeds, Inc., St. Joseph, Mo.

[21] Appl. No.: 616,022

[22] Filed: Nov. 21, 1990

[51] Int. Cl.[6] ...................... A01N 63/00; C05F 11/08; C12N 1/21; C12N 15/00

[52] U.S. Cl. ................................ 424/93.2; 435/252.2; 435/172.3; 435/878; 935/64; 71/7; 47/57.6; 47/58

[58] Field of Search ............... 435/252.2, 252.3, 172.3, 435/878, 64; 800/200; 424/93 A, 93 D, 93.2, 93.4; 71/6, 7; 47/58, 57.6; 44/57.6

[56] References Cited

U.S. PATENT DOCUMENTS 4,782,022 11/1988 Puhler et al. ..................... 435/172.3
5,077,209 12/1991 O'Gara ............................ 435/172.3

OTHER PUBLICATIONS

Sprent, J. I. et al. 1990. "Nitrogen Fixing Organisms". Chapman and Hall, New York, pp. 30–65.

Watson, R. J. et al. 1988. J. Bacteriol. vol. 170 p. 927–934.

Watson, R. J. 1990. Molecular Plant–Microbe Interactions, vol. 3, No. 3, pp. 174–181.

Engelke, T. et al. 1989. J. Bacteriol. vol. 171 pp. 5551–5560.

Roughley R. J. et al. 1982. *Nitrogen Fixation in Legumes,* pp. 193–209.

FIscher, H.–M. et al. 1986 *EMBO Joournal vol. 5, pp. 1165–1173.*

Jagadish, M. N. et al. 1985, *MGG* vol. 199 pp. 249–255.

Carbin, D. et al. 1983. Proc. *Natl. Acad. Sci. USA* vol. 80 pp. 3005–3009.

Ronson et al., Journal of Bacteriology, Dec. 1984, vol. 160, No. 3, pp. 903–909.

Ronson et al., Nucleic Acids Research, Nov. 1987, vol. 15, pp. 7921–7934.

*Primary Examiner*—Mary E. Mosher
*Attorney, Agent, or Firm*—Kinney & Lange

[57] ABSTRACT

A bacterial inoculum including a rhizospheric bacterium with increased dicarboxylic acid membrane permease activity.

14 Claims, 20 Drawing Sheets

```
      U   C
   A         C
    C       A
       U . A
       G . C
       C . G
       C . G
       C . G
       G . C
       G . C
CUGCAGC.GUUUCUCUUUUC
```

```
        10        20        30        40        50        60
GTTGCAGGGGCAGGGAAGGCCACAATTTCTGCGACACGGACATGGCGGATTTGTGCATTTTTCTGCACGA

        80        90       100       110       120       130
AACGCAAATGGATTTGTGCGGATTTCCGCATTGCTTAGTTAGTTGTTAGCAGTCTCGTAAATTTTTCATT

       150       160       170       180       190       200
AATAAATTCAATCGGTTGGTTGGCGACTTAAAACTGGCACGGCGATTGCGAAGGAGGTGGCAACAACGGC

       220       230       240       250       260       270
TGAGCTGTTGGACTTGAAGCGAACGGCTCGGGAGGCCGGAGTTCGTTCCGGACGAGCCACACTAGGAGGA

       290       300       310       320       330       340
CATCATGATCGCAGCACCACTCGATGCAGTCGCAGGCAGCAAGGGCAAGAAGCCCTTTTATAGCCATCTT
    MetIleAlaAlaProLeuAspAlaValAlaGlySerLysGlyLysLysProPheTyrSerHisLeu
      1           5              10              15              20

       360       370       380       390       400       410
TACGTTCAGGTTCTCGTGGCCATCGCTGCGGGTATCCTTCTCGGTCATTTCTATCCCGAACTCGGCACCC
TyrValGinValLeuValAlaIleAlaAlaGlyIleLeuLeuGlyHisPheTyrProGluLeuGlyThrG
      25             30              35              40              45

       430       440       450       460       470       480
AGCTGAAGCCGCTCGGCGATGCCTTCATCAAGCTCGTCAAGATGATCATTGCGCCGGTGATCTTTCTGAC
lnLeuLysProLeuGlyAspAlaPheIleLysLeuValLysMetIleIleAlaProValIlePheLeuTh
             50              55              60              65

       500       510       520       530       540       550
GGTTGCGACCGGCATTGCCGGCATGAGCGACCTGCAGAAGGTCGGCCGCGTCGCCGGCAAGGCGATGCTG
rValAlaThrGlyIleAlaGlyMetSerAspLeuGlnLysValGlyArgValAlaGlyLysAlaMetLeu
   70            75              80              85              90

       570       580       590       600       610       620
TACTTCCTGACCTTCTCGACATTGGCGCTCATCATCGGCCTGATCGTCGCCAATGTCGTCCAGCCAGGCG
TyrPheLeuThrPheSerThrLeuAlaLeuIleIleGlyLeuIleValAlaAsnValValGlnProGlyA
      95             100             105             110             115

       640       650       660       670       680       690
CCGGCATGAACATCGATCCGGCCTCGCTGGATCCGGCCGCCGTCGCCACCTTTGCCGCCAAGGCGCATGA
laGlyMetAsnIleAspProAlaSerLeuAspProAlaAlaValAlaThrPheAlaAlaLysAlaHisGl
             120             125             130             135

       710       720       730       740       750       760
GCAGAGCATCGTCGGCTTCCTCACCAACATCATCCCGACGACGATTGTCGGCGCCTTTGCCGATGGCGAT
uGlnSerIleValGlyPheLeuThrAsnIleIleProThrThrIleValGlyAlaPheAlaAspGlyAsp
 140             145             150             155             160

       780       790       800       810       820       830
ATTCTGCAGGTTCTGTTCTTCTCGGTGCTCTTCGGCATCGCGCTCGCCATGGTCGGCGAAAAGGGCGAGC
IleLeuGlnValLeuPhePheSerValLeuPheGlyIleAlaLeuAlaMetValGlyGluLysGlyGluG
      165            170             175             180             185

       850       860       870       880       890       900
AGGTCGTCAACTTCCTCAATTCCCTGACGGCTCCCGTGTTCAAGCTCGTCGCCATCCTCATGAAGGCTGC
lnValValAsnPheLeuAsnSerLeuThrAlaProValPheLysLeuValAlaIleLeuMetLysAlaAl
             190             195             200             205
```

*Fig. 2A*

```
        920       930       940       950       960       970
CCCGATCGGCGCCTTCGGCGCCATGGCATTCACCATCGGCAAGTACGGCGTCGGATCGATCGCCAACCTT
aProIleGlyAlaPheGlyAlaMetAlaPheThrIleGlyLysTyrGlyValGlySerIleAlaAsnLeu
 210            215            220            225            230

        990      1000      1010      1020      1030      1040
GCCATGCTAATCGGCACTTTCTACATCACGTCTCTGCTCTTCGTCTTCATCGTTCTCGGTGCTGTTGCCC
AlaMetLeuIleGlyThrPheTyrIleThrSerLeuLeuPheValPheIleValLeuGlyAlaValAlaA
      235            240            245            250            255

       1060      1070      1080      1090      1100      1110
GCTACAACGGATTCTCGATCGTGGCGCTGCTGCGCTACATCAAGGAAGAACTGCTGCTGGTCCTCGGCAC
rgTyrAsnGlyPheSerIleValAlaLeuLeuArgTyrIleLysGluGluLeuLeuLeuValLeuGlyTh
           260            265            270            275

       1130      1140      1150      1160      1170      1180
CTCGTCTTCGGAAGCCGCACTTCCGGGGCTGATGAACAAGATGGAAAAGGCCGGTTGCAAGCGCTCGGTC
rSerSerSerGluAlaAlaLeuProGlyLeuMetAsnLysMetGluLysAlaGlyCysLysArgSerVal
 280            285            290            295            300

       1200      1210      1220      1230      1240      1250
GTCGGCCTCGTCATCCCGACCGGCTATTCCTTCAATCTTGACGGCACCAACATCTACATGACGCTGGCAG
ValGlyLeuValIleProThrGlyTyrSerPheAsnLeuAspGlyThrAsnIleTyrMetThrLeuAlaA
      305            310            315            320            325

       1270      1280      1290      1300      1310      1320
CGCTGTTCATTGCTCAGGCAACCGGCATCCATCTCTCCTGGGGTGACCAGATCCTGCTGCTGCTGGTGGC
laLeuPheIleAlaGlnAlaThrGlyIleHisLeuSerTrpGlyAspGlnIleLeuLeuLeuLeuValAl
           330            335            340            345

       1340      1350      1360      1370      1380      1390
GATGCTGAGCTCGAAGGGTGCCGCAGGCATCACCGGCGCCGGCTTCATCACGCTTGCCGCAACGCTCTCC
aMetLeuSerSerLysGlyAlaAlaGlyIleThrGlyAlaGlyPheIleThrLeuAlaAlaThrLeuSer
 350            355            360            365            370

       1410      1420      1430      1440      1450      1460
GTCGTCCCATCCGTGCCGGTCGCTGGCATGGCGCTCATTCTCGGCATCGACCGTTTCATGTCGGAATGCC
ValValProSerValProValAlaGlyMetAlaLeuIleLeuGlyIleAspArgPheMetSerGluCysA
      375            380            385            390            395

       1480      1490      1500      1510      1520      1530
GGGCGCTGACCAACCTCGTCGGCAATGCGGTGGCGACGATCGTCGTGGCACGTTGGGAAAACGAGCTGGA
rgAlaLeuThrAsnLeuValGlyAsnAlaValAlaThrIleValValAlaArgTrpGluAsnGluLeuAs
           400            405            410            415

       1550      1560      1570      1580      1590      1600
TACGGTGCAACTCGCCGCAGCACTGGGCGGCCAGACCGGAGAGGATACTTCGGCTGCCGGGCTGCAGCCG
pThrValGlnLeuAlaAlaAlaLeuGlyGlyGlnThrGlyGluAspThrSerAlaAlaGlyLeuGlnPro
 420            425            430            435            440

       1620      1630      1640      1650      1660      1670
GCCGAATAGTCAGCCGCTATCCCCTTATCCTTAGAAACCCTGCAGCGGCCCGTCATCCAACGGGCCGTTT
AlaGluEnd
      445

       1690      1700
CTCTTTTCGGCTTCAGCTGCGA
```

Fig. 2B

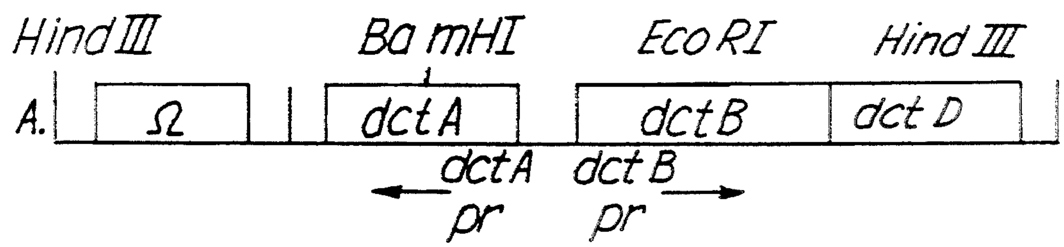
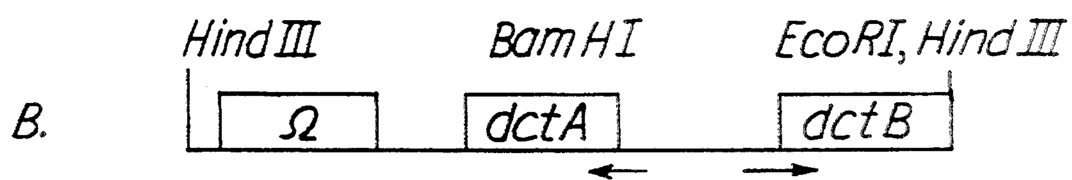
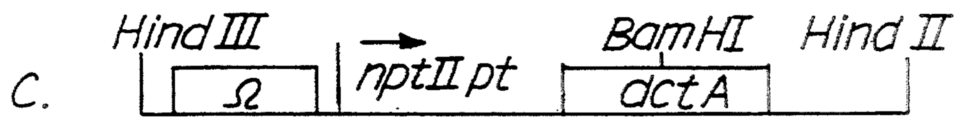
Hind III
Bam HI
Hind II
D.
Ω
Rm fixA pr
dctA
Fig. 4

Bgl II Sph I

AGATCTGCGAGATTTTCAGGAGCTAAGGAAGTAAGCAT

RMB 7000 (ORIGINAL Tn5-induced ino mutant of Rm 1021)

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 1702
( B ) TYPE: nucleic acid
( C ) STRANDEDNESS: single
( D ) TOPOLOGY: linear ( x i ) SEQUENCE DESCRIPTION: SEQUENCE ID NO: 1:

```
GTTGCAGGGG CAGGGAAGGC CACAATTTCT GCGACACGGA CATGGCGGAT TTGTGCATTT   60

TTCTGCACGA AACGCAAATG GATTTGTGCG GATTTCCGCA TTGCTTAGTT AGTTGTTAGC  120

AGTCTCGTAA ATTTTTCATT AATAAATTCA ATCGGTTGGT TGGCGACTTA AAACTGGCAC  180

GGCGATTGCG AAGGAGGTGG CAACAACGGC TGAGCTGTTG GACTTGAAGC GAACGGCTCG  240

GGAGGCCGGA GTTCGTTCCG GACGAGCCAC ACTAGGAGGA CATCATG ATC GCA GCA    296
                                                Met Ile Ala Ala
                                                  1

CCA CTC GAT GCA GTC GCA GGC AGC AAG GGC AAG AAG CCC TTT TAT AGC    344
Pro Leu Asp Ala Val Ala Gly Ser Lys Gly Lys Lys Pro Phe Tyr Ser
  5                  10                  15                  20

CAT CTT TAC GTT CAG GTT CTC GTG GCC ATC GCT GCG GGT ATC CTT CTC    392
His Leu Tyr Val Gln Val Leu Val Ala Ile Ala Ala Gly Ile Leu Leu
                 25                  30                  35

GGT CAT TTC TAT CCC GAA CTC GGC ACC CAG CTG AAG CCG CTC GGC GAT    440
Gly His Phe Tyr Pro Glu Leu Gly Thr Gln Leu Lys Pro Leu Gly Asp
             40                  45                  50

GCC TTC ATC AAG CTC GTC AAG ATG ATC ATT GCG CCG GTG ATC TTT CTG    488
Ala Phe Ile Lys Leu Val Lys Met Ile Ile Ala Pro Val Ile Phe Leu
         55                  60                  65

ACG GTT GCG ACC GGC ATT GCC GGC ATG AGC GAC CTG CAG AAG GTC GGC    536
Thr Val Ala Thr Gly Ile Ala Gly Met Ser Asp Leu Gln Lys Val Gly
     70                  75                  80

CGC GTC GCC GGC AAG GCG ATG CTG TAC TTC CTG ACC TTC TCG ACA TTG    584
Arg Val Ala Gly Lys Ala Met Leu Tyr Phe Leu Thr Phe Ser Thr Leu
 85                  90                  95                 100

GCG CTC ATC ATC GGC CTG ATC GTC GCC AAT GTC GTC CAG CCA GGC GCC    632
Ala Leu Ile Ile Gly Leu Ile Val Ala Asn Val Val Gln Pro Gly Ala
                105                 110                 115

GGC ATG AAC ATC GAT CCG GCC TCG CTG GAT CCG GCC GCC GTC GCC ACC    680
Gly Met Asn Ile Asp Pro Ala Ser Leu Asp Pro Ala Ala Val Ala Thr
            120                 125                 130

TTT GCC GCC AAG GCG CAT GAG CAG AGC ATC GTC GGC TTC CTC ACC AAC    728
```

-continued

```
Phe Ala Ala Lys Ala His Glu Gln Ser Ile Val Gly Phe Leu Thr Asn
        135                 140                 145

ATC ATC CCG ACG ACG ATT GTC GGC GCC TTT GCC GAT GGC GAT ATT CTG      776
Ile Ile Pro Thr Thr Ile Val Gly Ala Phe Ala Asp Gly Asp Ile Leu
    150                 155                 160

CAG GTT CTG TTC TTC TCG GTG CTC TTC GGC ATC GCG CTC GCC ATG GTC      824
Gln Val Leu Phe Phe Ser Val Leu Phe Gly Ile Ala Leu Ala Met Val
165                 170                 175                 180

GGC GAA AAG GGC GAG CAG GTC GTC AAC TTC CTC AAT TCC CTG ACG GCT      872
Gly Glu Lys Gly Glu Gln Val Val Asn Phe Leu Asn Ser Leu Thr Ala
                185                 190                 195

CCC GTG TTC AAG CTC GTC GCC ATC CTC ATG AAG GCT GCC CCG ATC GGC      920
Pro Val Phe Lys Leu Val Ala Ile Leu Met Lys Ala Ala Pro Ile Gly
            200                 205                 210

GCC TTC GGC GCC ATG GCA TTC ACC ATC GGC AAG TAC GGC GTC GGA TCG      968
Ala Phe Gly Ala Met Ala Phe Thr Ile Gly Lys Tyr Gly Val Gly Ser
        215                 220                 225

ATC GCC AAC CTT GCC ATG CTA ATC GGC ACT TTC TAC ATC ACG TCT CTG     1016
Ile Ala Asn Leu Ala Met Leu Ile Gly Thr Phe Tyr Ile Thr Ser Leu
    230                 235                 240

CTC TTC GTC TTC ATC GTT CTC GGT GCT GTT GCC CGC TAC AAC GGA TTC     1064
Leu Phe Val Phe Ile Val Leu Gly Ala Val Ala Arg Tyr Asn Gly Phe
245                 250                 255                 260

TCG ATC GTG GCG CTG CTG CGC TAC ATC AAG GAA GAA CTG CTG CTG GTC     1112
Ser Ile Val Ala Leu Leu Arg Tyr Ile Lys Glu Glu Leu Leu Leu Val
                265                 270                 275

CTC GGC ACC TCG TCT TCG GAA GCC GCA CTT CCG GGG CTG ATG AAC AAG     1160
Leu Gly Thr Ser Ser Ser Glu Ala Ala Leu Pro Gly Leu Met Asn Lys
            280                 285                 290

ATG GAA AAG GCC GGT TGC AAG CGC TCG GTC GTC GGC CTC GTC ATC CCG     1208
Met Glu Lys Ala Gly Cys Lys Arg Ser Val Val Gly Leu Val Ile Pro
        295                 300                 305

ACC GGC TAT TCC TTC AAT CTT GAC GGC ACC AAC ATC TAC ATG ACG CTG     1256
Thr Gly Tyr Ser Phe Asn Leu Asp Gly Thr Asn Ile Tyr Met Thr Leu
    310                 315                 320

GCA GCG CTG TTC ATT GCT CAG GCA ACC GGC ATC CAT CTC TCC TGG GGT     1304
Ala Ala Leu Phe Ile Ala Gln Ala Thr Gly Ile His Leu Ser Trp Gly
325                 330                 335                 340

GAC CAG ATC CTG CTG CTG CTG GTG GCG ATG CTG AGC TCG AAG GGT GCC     1352
Asp Gln Ile Leu Leu Leu Leu Val Ala Met Leu Ser Ser Lys Gly Ala
                345                 350                 355

GCA GGC ATC ACC GGC GCC GGC TTC ATC ACG CTT GCC GCA ACG CTC TCC     1400
Ala Gly Ile Thr Gly Ala Gly Phe Ile Thr Leu Ala Ala Thr Leu Ser
            360                 365                 370

GTC GTC CCA TCC GTG CCG GTC GCT GGC ATG GCG CTC ATT CTC GGC ATC     1448
Val Val Pro Ser Val Pro Val Ala Gly Met Ala Leu Ile Leu Gly Ile
        375                 380                 385

GAC CGT TTC ATG TCG GAA TGC CGG GCG CTG ACC AAC CTC GTC GGC AAT     1496
Asp Arg Phe Met Ser Glu Cys Arg Ala Leu Thr Asn Leu Val Gly Asn
    390                 395                 400

GCG GTG GCG ACG ATC GTC GTG GCA CGT TGG GAA AAC GAG CTG GAT ACG     1544
Ala Val Ala Thr Ile Val Val Ala Arg Trp Glu Asn Glu Leu Asp Thr
405                 410                 415                 420

GTG CAA CTC GCC GCA GCA CTG GGC GGC CAG ACC GGA GAG GAT ACT TCG     1592
Val Gln Leu Ala Ala Ala Leu Gly Gly Gln Thr Gly Glu Asp Thr Ser
                425                 430                 435

GCT GCC GGG CTG CAG CCG GCC GAA TAG TCAGCCGCTA TCCCCTTATC            1639
Ala Ala Gly Leu Gln Pro Ala Glu End
            440                 445

CTTAGAAACC CTGCAGCGGC CCGTCATCCA ACGGGCCGTT TCTCTTTTCG GCTTCAGCTG   1699

CGA                                                                 1702
```

-continued ( 2 ) INFORMATION FOR SEQ ID NO:2:

( i ) SEQUENCE CHARACTERISTICS:
( A ) LENGTH: 39
( B ) TYPE: nucleic acid
( C ) STRANDEDNESS: single
( D ) TOPOLOGY: linear ( x i ) SEQUENCE DESCRIPTION: SEQUENCE ID NO: 2:

CUGCAGCGGC CCGUCAUCCA ACGGGCCGUU UCUCUUUC 39

( 2 ) INFORMATION FOR SEQ ID NO:3:

( i ) SEQUENCE CHARACTERISTICS:
( A ) LENGTH: 39
( B ) TYPE: nucleic acid
( C ) STRANDEDNESS: single
( D ) TOPOLOGY: linear ( x i ) SEQUENCE DESCRIPTION: SEQUENCE ID NO: 3:
AGATCTGCGA GATTTTCAGG AGCTAAGGAA GTAAGCATG 39

( 2 ) INFORMATION FOR SEQ ID NO:4:

( i ) SEQUENCE CHARACTERISTICS:
( A ) LENGTH: 191
( B ) TYPE: nucleic acid
( C ) STRANDEDNESS: single
( D ) TOPOLOGY: linear ( x i ) SEQUENCE DESCRIPTION: SEQUENCE ID NO: 4:

GGTACCCATG CAAGGAGATG GCGCCCAACA GTCCCCCGGC CACGGGCCTG CCACCATACC 60

CACGCCGAAA CAAGCGCTGA TGAGCCCGAA GTGGCGAGCC CGATCTTCCC CATCGGTGAT 120

GTCGGCGATA TAGGCGCCAG CAACCGCACC TGTGGCGCCG GTGATGCCGG CCACGATGCG 180

TCCGGCGTAG A 191

( 2 ) INFORMATION FOR SEQ ID NO:5:

( i ) SEQUENCE CHARACTERISTICS:
( A ) LENGTH: 305
( B ) TYPE: nucleic acid
( C ) STRANDEDNESS: single
( D ) TOPOLOGY: linear ( x i ) SEQUENCE DESCRIPTION: SEQUENCE ID NO: 5:

CATCTAGCGC GCGAGATCGC AGTACATTAC ATCGGAGGTT CACCACCTCT AGGTTTCAAT 60

AACTATGAAG GATTGGAAGC CAGACTTGCG GCCTGCTTCC GCCTTACACC GCAGCGTTGC 120

TGTCGCCCAT AAACTCAAAA ACTCCGCCGT GAATTTCACG CGCGGCCCGC TTGTTCCATT 180

TCGACACCGC CAAACCAAGA GTCCCTCGCA AAGGGGAGTG TCGGATTCCC AACAACAGCC 240

CCTCACCGTA CAAGTCCCGC TAAGAAACTG TTGTTGTTCT ACTTTTACTG CTCATGAGAC 300

CTGG 305

( 2 ) INFORMATION FOR SEQ ID NO:6:

( i ) SEQUENCE CHARACTERISTICS:
( A ) LENGTH: 23
( B ) TYPE: nucleic acid
( C ) STRANDEDNESS: single
( D ) TOPOLOGY: linear ( x i ) SEQUENCE DESCRIPTION: SEQUENCE ID NO: 6:

GCATGCCGGT TGCAAAGTCT TGG 23

( 2 ) INFORMATION FOR SEQ ID NO:7:

( i ) SEQUENCE CHARACTERISTICS:
( A ) LENGTH: 21

-continued ( B ) TYPE: nucleic acid
( C ) STRANDEDNESS: single
( D ) TOPOLOGY: linear ( x i ) SEQUENCE DESCRIPTION: SEQUENCE ID NO: 7:

```
CCGGTTGCAA AGTCTTGGGGG                                                    21
```

( 2 ) INFORMATION FOR SEQ ID NO:8:

( i ) SEQUENCE CHARACTERISTICS:
( A ) LENGTH: 66
( B ) TYPE: nucleic acid
( C ) STRANDEDNESS: single
( D ) TOPOLOGY: linear ( x i ) SEQUENCE DESCRIPTION: SEQUENCE ID NO: 8:

```
CGCGCATGCT GTTGCGCATT CATGTGTCCG AACAACCGAA ATAGCTTAAA CAACAAAGGA    60

AGCAAG                                                               66
```

( 2 ) INFORMATION FOR SEQ ID NO:9:

( i ) SEQUENCE CHARACTERISTICS:
( A ) LENGTH: 1620
( B ) TYPE: nucleic acid
( C ) STRANDEDNESS: single
( D ) TOPOLOGY: linear ( x i ) SEQUENCE DESCRIPTION: SEQUENCE ID NO: 9:

```
CGC AAA CAG GAC AAG CGC TCC GCC GAA ATT TAC AGC ATA TCA AAG GCT    48
Arg Lys Gln Asp Lys Arg Ser Ala Glu Ile Tyr Ser Ile Ser Lys Ala
                5                   10                  15

TG ATG GCC CCC CAC TCG TCT TGA GAC CAC GCT TAA CAA TTT CGT GAA     96
Leu Met Ala Pro Thr Arg Leu Glu Thr Thr Leu Asn Asn Phe Val Asn
            20                  25                  30

TAC CCT CTC TTT GAT TCT GCG CAT GCG CCG CGG CGG ACT CGA GAT TCC   144
Thr Leu Ser Leu Ile Leu Arg Met Arg Arg Gly Gly Leu Glu Ile Pro
        35                  40                  45

GGC GTC GGA AGG AGA GAC AAA GAT AAC AGC GGC TAC CCG CAA CAG CGG   192
Ala Ser Glu Gly Glu Thr Lys Ile Thr Ala Ala Thr Arg Asn Ser Gly
    50                  55                  60

GTC TCC TTC TGC CGC TGA TTA TAC TGT ACC AAA GGC CGC AAT AGA CCA   240
Ser Ala Ala Asp Tyr Thr Val Pro Lys Ala Ala Ile Asp Gln Val Met
65                  70                  75                  80

AGT CAT GAC TGC CGG GCG GCT GGT CGT ACC AGA CGT TTG CAA CTC TGA   288
Thr Ala Gly Arg Leu Val Val Pro Asp Val Cys Asn Ser Glu Leu Phe
                85                  90                  95

GCT GTT CAA GGA TCA GAT AAA ATG GCG CGG AAT TGG TCC GAC TGC CTT   336
Lys Asp Gln Ile Lys Met Arg Gly Ile Gly Pro Thr Ala Phe Ile Ala
            100                 105                 110

CAT CGC TGC GGC GGT GGA GGT CGA TCA CGA AAC GGG CGG AAT GCT GTG   384
Ala Ala Val Glu Val Asp Ser Glu Thr Gly Gly Met Leu Val Phe Glu
        115                 120                 125

GTT CGA GTG CGC CGA AGA GTC CGA TTA TGA TTA TGA GGA GGA GGT ACA   432
Cys Ala Glu Glu Ser Asp Tyr Asp Tyr Glu Glu Glu Val Thr Phe Leu
    130                 135                 140

CTT TCT TTC TAT GGC CGC CAA TCT TGC GGG GAG GGC CAT TCG GCT TCA   480
Ser Tyr Ala Ala Asn Leu Ala Gly Arg Ala Ile Arg Leu Ser Arg Thr
145                 150                 155                 160

TCG CAC AAT CAG CAG GCG TGA GCG GAC ATT TGC CGA AGA GCA GCA AGA   528
Ile Ser Arg Arg Glu Arg Thr Phe Ala Glu Glu Gln Gln Glu Gln Gln
                165                 170                 175

ACA ACA GAA TTC ACG TGA TGA GCA GAG CCA GAG TTC CGC CCG CCA GCG   576
Asn Ser Arg Asp Glu Gln Ser Gln Ser Ser Ala Arg Gln Arg Leu Leu
            180                 185                 190

GCT GCT CAA GAA TGA CGG GAT CAT CGG GGA AAG TAC CGC CCT CAT GAC   624
Lys Asn Asp Gly Ile Ile Gly Glu Ser Thr Ala Leu Met Thr Ala Val
```

-continued

```
        195                             200                             205

GGC GGT AGA TAC CGC CAA AGT CAT GGC AGA GAC CAA TTC AAT CGT TCT        672
Asp Thr Ala Lys Val Met Ala Glu Thr Asn Ser Ile Val Leu Leu Arg
    210                     215                     220

CCT TAG GGG AGA AAC AGG AAC TGG CAA GGA ATG CTT TGC GAA GCT AAT        720
Gly Glu Thr Gly Thr Gly Lys Glu Cys Phe Ala Lys Leu Ile Pro Gln
225                 230                     235                 240

CCA CCA GCA TTC GAC TCG GCA AAA AAA GCC CTT CAT CAA GTT CAA TTG        768
Ala Ser Thr Arg Gln Lys Lys Pro Phe Ile Lys Phe Asn Cys Pro Ala
                245                     250                 255

CCC CGC GGT GTC TGA GAG CCT TCT CGA ATC AGA GCT GTT TGG ACA TGA        816
Leu Ser Glu Ser Leu Leu Glu Ser Glu Leu Phe Gly Thr Glu Lys Gly
            260                 265                 270

GAA AGG TGC GTT CAC CGG GGC TAT TGC TCA AAG AGT AGG CCG TTT CGA        864
Ala Phe Thr Gly Ala Ile Ala Gln Arg Val Gly Arg Phe Glu Ser Ala
        275                     280                     285

ATC GGC GAA TGG CGG AAG GTT GCT GCT CGA TGA AAT CGG CGA GAT TCC        912
Asn Gly Gly Thr Leu Leu Leu Asp Glu Ile Gly Glu Ile Pro Pro Ala
    290                     295                     300

CCC GGC GTT CCA AGC AAA ACT GCT ACG CGT AAT ACA GGA AGG TGA ATT        960
Phe Gln Ala Lys Leu Leu Arg Val Ile Gln Glu Gly Glu Phe Glu Arg
305                 310                     315                 320

TGA GGG AGT GGG GGG CAC AAA GAC GCT GAA AGT CGA CGT CCG GCT CAT       1008
Val Gly Gly Thr Lys Thr Leu Lys Val Asp Val Arg Leu Ile Phe Ala
                325                     330                 335

ATT CGC CAC AAA TAA GGA TCT CGA AAT GGG GGT CCA GAA TGG GGA GTT       1056
Thr Asn Lys Asp Leu Glu Met Ala Val Gln Asn Gly Glu Phe Arg Glu
            340                     345                 350

CAG GGA AGA CCT TTA CTA CCG CAT CAG CGG GGT GCC GCT CAT TTT GGG       1104
Asp Leu Tyr Tyr Arg Ile Ser Gly Val Pro Leu Ile Leu Pro Pro Leu
        355                     360                     365

GGG GCT TAG GCA GGG GGA CGG TGA CAT TCC GCT CCT TGC AAG AGC ATT       1152
Arg Pro Arg Asp Gly Asp Ile Pro Leu Leu Ala Arg Ala Phe Leu Gln
    370                     375                     380

CCT TCA GCG GTT CAA CGA AGA GAA CGG TCG TGA TCT CCA TTT GGG GGG       1200
Arg Phe Asn Glu Glu Asn Gly Arg Asp Leu Pro Phe Ala Pro Ser Ala
385                 390                     495                 400

GTC TGG GCT TGA CCA CTT GTC GAA GTG CAA GTT CCC TGG AAA CGT TCG       1248
Leu Asp Pro Leu Ser Lys Cys Lys Phe Pro Gly Asn Val Arg Glu Leu
                405                     410                 415

CGA GCT GGA AAA CTG TGT GGG GAG GAC TGC AAC TCT GGG CAG GTC AAA       1296
Glu Asn Cys Val Arg Arg Thr Ala Thr Leu Ala Arg Ser Lys Thr Ile
            420                     425                 430

GAC GAT CAC TTC GTC AGA TTT GGC CTG CCA AAG GGA CCA GTG TTT TTC       1344
Thr Ser Ser Asp Phe Ala Cys Gln Thr Asp Gln Cys Phe Ser Ser Arg
        435                     440                     445

TTC TCG CCT CTG GAA AGG GGT TCA CTG TTC GCA TGG CCA CAT TGA GAT       1392
Leu Leu Lys Gly Val Ser Cys Ser Ala Gly Pro Ile Glu Ile Asp Ala
    450                     455                     460

CGA TGG GGG GGG GGG TAC AAC ACC GTT GCT GGG AGG GGC AGC CAA TGA       1440
Pro Ala Gly Thr Thr Pro Leu Leu Gly Ala Pro Ala Asn Asp Val Pro
465                 470                     475                 480

CGT TGG GCC GAA AGA GGG GGG ATG GGC AGG AGT GGC ATC CAA TCT GAT       1488
Pro Lys Glu Pro Gly Ser Ala Gly Val Ala Ser Asn Leu Ile Glu Arg
                485                     490                 495

CGA GGG GGA GGG GTT GAT CAG TGG GCT GGA GGA GGG GGG TTG GAA TCA       1536
Asp Arg Leu Ile Ser Ala Leu Glu Glu Ala Gly Leu Asn Gln Ala Lys
            500                     505                 510

GGC AAA GGC AGC TCG CAT CCT CGA AAA AAG GGG GGG GCA GGT GGG GTA       1584
Ala Ala Arg Ile Leu Glu Lys Thr Pro Arg Gln Val Gly Tyr Ala Leu
```

-continued

```
      515                          520                          525

TGC TCT AGG TGG GCA TGG TGT GGA CGT GAG AAA GCT                                    1620
Arg Arg His Gly Val Asp Val Arg Lys Leu
    530                 535
```

( 2 ) INFORMATION FOR SEQ ID NO:10:

( i ) SEQUENCE CHARACTERISTICS:
( A ) LENGTH: 23
( B ) TYPE: nucleic acid
( C ) STRANDEDNESS: single
( D ) TOPOLOGY: linear ( x i ) SEQUENCE DESCRIPTION: SEQUENCE ID NO: 10:

CTAAGACTAG TCGGTGAGAT AAA ( 2 ) INFORMATION FOR SEQ ID NO:11:

( i ) SEQUENCE CHARACTERISTICS:
( A ) LENGTH: 23
( B ) TYPE: nucleic acid
( C ) STRANDEDNESS: single
( D ) TOPOLOGY: linear ( x i ) SEQUENCE DESCRIPTION: SEQUENCE ID NO: 11:

GGCCGTCGCA GATCGCTGGT ACC 23

RHIZOSHERIC BACTERIA

This invention relates to the genetic engineering of agriculturally useful microorganisms.

BACKGROUND OF THE INVENTION

The identification or production of microbial strains with enhanced biological activity, e.g., strains with enhanced nitrogen fixation capability, or enhanced pesticidal activity, is an important goal in agricultural biotechnology. In many agricultural applications an improved microbial strain is added to the soil and thus must compete with native free-living microbes for growth and nutrients. Even though a microbe possesses a useful biological activity, failure to compete with native organisms will most often render it ineffective in the field. For example, displacement of established populations of *Bradyrhizobium japonicum* by inoculation with strains that are efficient nitrogen fixers has proven difficult (Triplett (1990) Molec. Plant Microb. Interactions 3:199–206). Efforts to improve the competitiveness of specific microorganisms in agricultural settings have included searches for naturally occurring strains which possess a competitive advantage, Tn5 mutagenesis-selection experiments, and experiments designed to exploit the effects of various naturally occurring indigenous plasmids.

SUMMARY OF THE INVENTION

In general the invention features a bacterial inoculum including a rhizospheric bacterium with increased dicarboxylic acid membrane permease activity. In preferred embodiments the rhizospheric bacterium is transformed with a DNA sequence which increases the dicarboxylic acid membrane permease (DMP) activity of the bacterium, e.g., a sequence which encodes dicarboxylic acid membrane permease, or any or all of: a sequence which encodes the dctB gene product, a sequence which encodes the dctD gene product, or a sequence which encodes the dctA gene product.

In preferred embodiments the bacterium of the inoculum is transformed with a second DNA sequence, the second sequence conferring a desirable property on the bacterium e.g., a sequence which increases the capability of the bacterium to fix nitrogen e.g., a sequence encoding a nifA gene product.

In preferred embodiments of the inoculum the rhizospheric bacterium is capable of colonizing the rhizosphere of a soybean plant; the rhizospheric bacterium is in the genus Bradyrhizobium, and is preferably *Bradyrhizobium japonicum;* the rhizospheric bacterium is capable of colonizing the rhizosphere of an alfalfa plant; the rhizospheric bacterium is in the genus Rhizobium, and is preferably *Rhizobium meliloti;* the rhizospheric bacterium is capable of colonizing the rhizosphere of a clover plant; and the rhizospheric bacterium is *Rhizobium trifolii.*

In preferred embodiments the increase in dicarboxylic acid membrane permease activity increases the competitiveness of the rhizospheric bacterium; increases nodule occupancy of the rhizospheric bacterium; and increases the nitrogen fixing capacity of the rhizospheric bacterium.

In preferred embodiments: the ability of the rhizospheric bacterium to exert a plant growth promoting effect is increased; the rhizospheric bacterium is in the genus Pseudomonas; and in more preferred embodiments the ability of a Pseudomonas strain to exert a plant growth promoting effect is increased.

The invention also features a bacterial inoculum including a free living beneficial rhizospheric bacterium with increased dicarboxylic acid membrane permease activity. In preferred embodiments the free living beneficial rhizospheric bacterium is transformed with a DNA sequence which increases the dicarboxylic acid membrane permease (DMP) activity of the bacterium, e.g., a sequence which encodes dicarboxylic acid membrane permease, or any or all of: a sequence which encodes the dctB gene product, a sequence which encodes the dctD gene product, or a sequence which encodes the dctA gene product.

In preferred embodiments the bacterium of the inoculum is transformed with a second DNA sequence, the second sequence conferring a desirable property on the free living beneficial rhizospheric bacterium; the increase in dicarboxylic acid membrane permease activity increases the competitiveness of the free living beneficial rhizospheric bacterium; a plant growth promoting activity of the free living beneficial rhizospheric bacterium is increased; the free living beneficial rhizospheric bacterium is in the genus Pseudomonas, and more preferably the plant growth promoting activity of a Pseudomonad is increased.

The invention also features a seed product including a plant seed e.g., a legume seed, e.g., a soybean, alfalfa, or clover seed to which is adhered a cell of a rhizospheric bacterium with increased dicarboxylic acid membrane permease activity. In preferred embodiments the rhizospheric bacterium is transformed with a DNA sequence which increases the dicarboxylic acid membrane permease (DMP) activity of the bacterium, e.g., a sequence which encodes dicarboxylic acid membrane permease, or any or all of: a sequence which encodes the dctB gene product, a sequence which encodes the dctD gene product, or a sequence which encodes the dctA gene product.

In preferred embodiments the bacterium of the seed product is transformed with a second DNA sequence, the second sequence conferring a desirable property on the bacterium e.g., a sequence which increases the capability of the bacterium to fix nitrogen e.g., a sequence encoding a nifA gene product.

In preferred embodiments of the seed product the rhizospheric bacterium is capable of colonizing the rhizosphere of a soybean plant; the rhizospheric bacterium is in the genus Bradyrhizobium, and is preferably *Bradyrhizobium japonicum;* the rhizospheric bacterium is capable of colonizing the rhizosphere of an alfalfa plant; the rhizospheric bacterium is in the genus Rhizobium, and is preferably *Rhizobium meliloti;* the rhizospheric bacterium is capable of colonizing the rhizosphere of a clover plant; and the rhizospheric bacterium is *Rhizobium trifolii.*

In preferred embodiments the increase in dicarboxylic acid membrane permease activity increases the competitiveness of the rhizospheric bacterium; increases nodule occupancy of the rhizospheric bacterium; and increases the nitrogen fixing capacity of the rhizospheric bacterium.

In preferred embodiments: the ability of the rhizospheric bacterium to exert a plant growth promoting effect is increased; the rhizospheric bacterium is in the genus Pseudomonas; and in more preferred embodiments the ability of a Pseudomonas strain to exert a plant growth promoting effect is increased.

The invention also features a seed product including a plant seed to which is adhered a cell of a free living beneficial rhizospheric bacterium with increased dicarboxylic acid membrane permease activity. In preferred embodiments the free living beneficial rhizospheric bacterium is transformed with a DNA sequence which increases the dicarboxylic acid membrane permease (DMP) activity of the bacterium, e.g., a sequence which encodes dicarboxylic acid membrane permease, or any or all of: a sequence which encodes the dctB gene product, a sequence which encodes the dctD gene product, or a sequence which encodes the dctA gene product.

In preferred embodiments the bacterium of the seed product is transformed with a second DNA sequence, the second sequence conferring a desirable property on the free living beneficial rhizospheric bacterium; the increase in dicarboxylic acid membrane permease activity increases the competitiveness of the free living beneficial rhizospheric bacterium; a plant growth promoting activity of the free living beneficial rhizospheric bacterium is increased; the free living beneficial rhizospheric bacterium is in the genus Pseudomonas, and more preferably the plant growth promoting activity of the Pseudomonad is increased.

The invention also features a plant, e.g., a legume, e.g., a soybean, alfalfa, or clover plant, the rhizosphere of which includes a rhizospheric bacterium with increased dicarboxylic acid membrane permease activity. In preferred embodiments the rhizospheric bacterium is transformed with a DNA sequence which increases the dicarboxylic acid membrane permease activity of the rhizospheric bacterium, e.g., a DNA sequence which encodes dicarboxylic acid membrane permease; or any or all of: a DNA sequence which encodes the dctB gene product, a DNA sequence which encodes the dctD gene product, or a DNA sequence which encodes the dctA gene product.

In preferred embodiments the rhizospheric bacterium is transformed with a second DNA sequence, the second sequence conferring a desirable property on the bacterium. The second sequence can include, e.g., a sequence which increases the capability of the rhizospheric bacterium to fix nitrogen, e.g., a sequence which encodes a nif gene product, e.g., the nifA gene product.

In preferred embodiments the rhizospheric bacterium is capable of colonizing the rhizosphere of a soybean plant; the rhizospheric bacterium is in the genus Bradyrhizobium, and preferably *Bradyrhizobium japonicum;* the rhizospheric bacterium is capable of colonizing the rhizosphere of an alfalfa plant; the rhizospheric bacterium is a member of the genus Rhizobium, and is preferably *Rhizobium meliloti;* the said rhizospheric bacterium is capable of colonizing the rhizosphere of a clover plant; and the rhizospheric bacterium is *Rhizobium trifolii.*

In preferred embodiments the increase in dicarboxylic acid membrane permease activity increases the competitiveness of the rhizospheric bacterium; increases nodule occupancy by the rhizospheric bacterium; and increases the nitrogen fixing capacity of the rhizospheric bacterium.

In preferred embodiments the rhizospheric bacterium is a Pseudomonas strain, and in more preferred embodiments the ability of a Pseudomonas strain to exert a plant growth promoting effect is increased.

The invention also features a plant, the rhizosphere of which includes a free living beneficial rhizospheric bacterium with increased dicarboxylic acid membrane permease activity. In preferred embodiments the free living beneficial rhizospheric bacterium is transformed with a DNA sequence which increases the dicarboxylic acid membrane permease activity of the free living beneficial rhizospheric bacterium, e.g., a DNA sequence which encodes dicarboxylic acid membrane permease, or any or all of: a DNA sequence which encodes the dctB gene product, a DNA sequence which encodes the dctD gene product, a DNA sequence which encodes the dctA gene product.

In preferred embodiments the free living beneficial rhizospheric bacterium is transformed with a second DNA sequence, the second sequence conferring a desirable property on the bacterium.

In preferred embodiments the increase in dicarboxylic acid membrane permease activity increases the competitiveness of the free living beneficial rhizospheric bacterium; the ability of the free living beneficial rhizospheric bacterium to exert a plant growth promoting activity is increased; the free living beneficial rhizospheric bacterium is a Pseudomonad, preferably a Pseudomonad in which the ability to exert a plant growth promoting effect is increased.

The invention also features a plant growth substrate including a rhizospheric bacterium with increased dicarboxylic acid membrane permease activity. In preferred embodiments the rhizospheric bacterium can colonize the rhizosphere of a legume; is transformed with a DNA sequence which increases the dicarboxylic acid membrane permease activity of the rhizospheric bacterium, e.g., a sequence which encodes dicarboxylic acid membrane permease; or is transformed with any or all of: a sequence which encodes the dctB gene product, a sequence which encodes the dctD gene product, or a sequence which encodes the dctA gene product.

In preferred embodiments the rhizospheric bacterium is transformed with a second DNA sequence, the second sequence conferring a desirable property on the bacterium. The second sequence can include a sequence which increases the capability of the bacterium to fix nitrogen e.g., a sequence which encodes a nil gene product, e.g., the nifA gene product.

In preferred embodiments the rhizospheric bacterium is capable of colonizing the rhizosphere of a soybean plant; the rhizospheric bacterium is a member of the genus Bradyrhizobium, and preferably is *Bradyrhizobium japonicum;* the rhizospheric bacterium is capable of colonizing the rhizosphere of an alfalfa plant; the rhizospheric bacterium is a member of the genus Rhizobium, and is preferably *Rhizobium meliloti;* and the rhizospheric bacterium is capable of colonizing the rhizosphere of a clover plant; and the rhizospheric bacterium is *Rhizobium trifolii.*

In preferred embodiments: the ability of the rhizospheric bacterium to exert a plant growth promoting effect is increased; the rhizospheric bacterium is a member of the genus Pseudomonas and in more preferred embodiments the ability of the Pseudomonas strain to exert a plant growth promoting effect is increased.

In preferred embodiments the increase in dicarboxylic acid membrane permease activity increases the competitiveness of the rhizospheric bacterium; increases the ability of the bacterium to occupy a nodule; and increases the nitrogen fixing capacity of the bacterium.

The invention also features a plant growth substrate including a free living beneficial rhizospheric bacterium with increased dicarboxylic acid membrane permease activity. In preferred embodiments the free living beneficial rhizospheric bacterium is transformed with a DNA sequence which increases the dicarboxylic acid membrane permease activity of the rhizospheric bacterium, e.g., a sequence which encodes dicarboxylic acid membrane permease; or is transformed with any or all of: a sequence which encodes the dctB gene product, a sequence which encodes the dctD gene product, or a sequence which encodes the dctA gene product.

In preferred embodiments the free living beneficial rhizospheric bacterium is transformed with a second DNA sequence, the second sequence conferring a desirable property on the bacterium; a plant growth promoting activity of the free living beneficial rhizospheric bacterium is increased; and the free living beneficial rhizospheric bacterium is a Pseudomonad, and preferably a plant growth promoting activity of the Pseudomonad is increased; and the increase in dicarboxylic acid membrane permease activity increases the competitiveness of the free living beneficial rhizospheric bacterium.

The invention also features a rhizospheric bacterium with increased dicarboxylic acid membrane permease activity transformed with a DNA sequence which imparts a desirable property on the bacterium, the desirable property being other than dicarboxylic acid membrane permease activity. For example, the rhizospheric bacterium can be transformed with a DNA sequence which encodes a gene product which increases the ability of the bacterium to fix nitrogen, e.g., a nifA gene product.

The invention also features a mutant rhizospheric or free living beneficial rhizospheric bacterium with increased dicarboxylic acid membrane permease activity, the mutant being the result of a mutagenesis step and a selection step.

In preferred embodiments the mutant free living beneficial rhizospheric bacterium is transformed with a second DNA sequence which confers a desirable property on the free living beneficial rhizospheric bacterium; the increase in dicarboxylic acid membrane permease activity increases the competitiveness of the free living beneficial rhizospheric bacterium; and the increase in dicarboxylic acid permease increases the ability of the free living beneficial rhizospheric bacterium to exert a plant growth promoting effect on a plant.

The invention also features a free living beneficial rhizospheric bacterium with increased dicarboxylic acid membrane permease activity. In preferred embodiments the free living beneficial rhizospheric bacterium is transformed with a DNA sequence which increases the dicarboxylic acid membrane permease activity of the free living beneficial rhizospheric bacterium, e.g., a sequence which encodes dicarboxylic acid membrane permease; and a sequence which encodes any or all of: the dctA gene product, the dctB gene product, and the dctD gene product.

In preferred embodiments the free living beneficial rhizospheric bacterium is transformed with a second DNA sequence, the second sequence conferring a desirable property on the free living beneficial rhizospheric bacterium. In preferred embodiments the increase in dicarboxylic acid membrane permease activity increases the competitiveness of the free beneficial rhizospheric bacterium; and increases the ability of the free living beneficial rhizospheric bacterium to exert a plant growth promoting effect on a plant.

The invention also features a method of coating a seed with a rhizospheric bacterium or free living beneficial rhizospheric bacterium transformed with DNA which increases the activity of dicarboxylic acid permease in the bacterium, which includes contacting the seed with the bacterium. In preferred embodiments the method includes mixing the bacterium with a carrier.

The invention also includes a method of producing a plant including, contacting a seed with a rhizospheric bacterium or free living beneficial rhizospheric bacterium with increased dicarboxylic acid membrane permease activity and cultivating the seed to produce the plant.

The invention also includes a method of increasing the competitiveness of a free living beneficial rhizospheric bacterium including, increasing the activity of dicarboxylic acid membrane permease in the free living beneficial rhizospheric bacterium, e.g., by mutagenesis or by transforming the free living beneficial rhizospheric bacterium with a DNA sequence e.g., a DNA sequence which encodes dicarboxylic acid membrane permease, and contacting the free living beneficial rhizospheric bacterium with the rhizosphere of a plant.

In preferred embodiments the increased competitiveness results in an increase in the numbers of the free living beneficial rhizospheric bacterium present in the rhizosphere; and in an increase in the plant growth promoting activity of the free living beneficial rhizospheric bacterium.

The invention also features a method of increasing the ability of a rhizospheric bacterium or free living beneficial rhizospheric bacterium to exert a beneficial effect or plant growth promoting effect on a plant including: transforming the bacterium with a first DNA sequence (e.g., a DNA sequence which encodes dicarboxylic acid membrane permease; or a DNA sequence which encodes any or all of: the dctB gene product, the dctD gene product, or the dctA gene product) which increases the activity of dicarboxylic acid membrane permease in the bacterium; and transforming the bacterium with a second DNA sequence which imparts an additional desired trait on the rhizospheric bacterium.

In preferred embodiments the second DNA sequence encodes the product of a nif gene, e.g., a nifA gene product.

In preferred embodiments the ability of the bacterium to exert a beneficial effect is the result of increased competitiveness; the increased competitiveness results in an increase in nodule occupancy by the bacterium; the increased competitiveness results in an increase in nitrogen fixation by the bacterium; and the increased competitiveness results in an increase in the ability of the bacterium to exert a plant growth promoting effect.

The invention also features a bacterium of the genus Rhizobium, preferably *R. meliloti,* with exogenous DNA, preferably expressable DNA, more preferably encoding a desired gene product, e.g., a protein, e.g., dicarboxylic acid membrane permease, integrated at the P3 site of the bacterium.

Exogenous DNA, as used herein, means DNA from any source that normally resides at a different site than the one at which it is to be integrated into.

Bacterial inoculum, as used herein, refers to a preparation of bacteria suitable for application to seeds, plants, soils or other agricultural materials. It can be dried granulated bacteria, or bacteria combined with a carrier. A carrier may be a liquid or solid and is chosen, which is suitable for a given application, and is chosen by methods known to those skilled in the art. An inoculum can be applied by methods known to those skilled in the art, e.g., to seeds, to plants, or to soil which contains or will contain the seeds or plants.

Competitiveness, as used herein, refers to the ability of a given strain to compete with other strains for growth, e.g., for growth in the rhizosphere, or in the soil. A strain exhibits increased competitiveness if, in comparison with a control strain (e.g., the parent strain from which the strain was derived), the strain of interest has an increased growth rate when measured under specific conditions, e.g., when grown in the rhizosphere or when grown in soil in the presence of other organisms. A strain which constitutes a larger percentage of the microbial population under given conditions than would a control strain, e.g., the parental strain, exhibits increased competitiveness.

Nodule occupancy, as defined herein, means that a bacterium resides in a nodule. Increased nodule occupancy, as used herein, means that the percentage of the total number of nodules present on a plant that contain the bacterium is increased relative to what would be seen with a control strain, e.g., a parental strain, under similar conditions.

A free living beneficial rhizospheric bacterium, as used herein, means any bacterium which can colonize the rhizosphere and that is capable of exerting a beneficial effect on a plant in the free living form, i.e., the bacterium can exert a beneficial effect without nodulating a plant (e.g., without entering a symbiotic relationship such as is required for nodulating nitrogen fixing bacteria to exert their beneficial nitrogen fixing effect). The beneficial effect can be any effect that is desirable in a plant, e.g., the suppression of pests or an increase in the yield of the plant. Examples of free living beneficial rhizospheric bacteria include bacteria in the following genera: Pseudomonas, Xanthomonas, Bacillus, Streptomyces, Serratia, and Enterobacter.

A bacterium adhered to a seed, as used herein, means a bacterium associated with a seed by any means or mechanism which results in the bacterium and seed being in such proximity that upon planting and development of roots from the seed, the bacterium is able to enter the rhizosphere. For example, the bacterium may be carried in vermiculite, clay, or peat, and dusted onto the seed, with or without a sticking agent such as gum arabic, the bacterium may be mixed in a coating polymer, e.g., carboxymethyl cellulose, which is coated onto the seed, or the bacterium and seed may be encapsulated in a suitable material, for example biodegradable plastic.

Rhizospheric bacterium, as used herein, means any bacterium which can colonize the rhizosphere of a plant. Preferably, a rhizospheric bacterium is capable of exerting a beneficial effect on a plant, e.g., by fixing nitrogen, or by exerting a plant growth promoting effect. Examples of rhizospheric bacteria are bacteria in the following genera: Rhizobium, Bradyrhizobium, Pseudomonas, Xanthomonas, Bacillus, Streptomyces, Serratia, or Enterobacter.

Rhizosphere, as used herein, means an area in and around the roots of a plant wherein the presence or growth of a rhizosphere colonizing bacterium can affect the metabolism of the plant.

Plant growth substrate, as used herein, means a supporting substrate for the roots of a plant, e.g., soil, vermiculite, or a combination thereof. A plant growth substrate which includes a bacterium of the invention can be used to coat or dust a seed.

Biocidal, as used herein, refers to the ability to suppress the effect of an organism which is detrimental to a plant and preferably to kill the organism. This includes biocidal properties of the type exhibited by bacteria of the genus Pseudomonas.

A plant growth promoting effect, as used herein, is any beneficial effect exerted on a plant, e.g., a crop plant, by a free living (as opposed to in a nodule) rhizospheric bacterium. These beneficial effects include e.g., biocidal effects and effects that stem from the secretion of a hormone or other substance by the bacterium. Plant growth promoting effects do not include beneficial effects that are only asserted by bacteria in a symbiotic relationship with a plant.

Dicarboxylic acid membrane permease (DMP), as used herein, refers to heterologous DMP (i.e., DMP encoded by a sequence derived from an organism of a species other than that of an organism into which a DMP encoding sequence is transformed) or more preferably to homologous DMP (i.e., DMP encoded by a sequence derived from an organism of the same species at that into which DNA encoding the DMP is transformed). Increased DMP activity means increased with respect to a control strain, e.g., a parental strain.

Dicarboxylic acid membrane permease activity, as used herein, means the ability of the DMP to transport dicarboxylic acids into a bacterial cell.

Capable of exerting a beneficial effect on a plant, as used herein, means capable of exerting any effect, or resulting in any change in a characteristic of a plant, that is desirable in agriculture, e.g., increased yield, increased growth rates, or increased resistance to pests or other undesirable conditions or elements.

A rhizospheric bacterium with increased dicarboxylic acid membrane permease, as used herein, refers to a rhizospheric bacterium which has an increase in DMP activity as compared with a control strain, e.g., a parental strain. The increase can be generated by methods known to those skilled in the art, e.g., by mutagenizing a parental strain then selecting for mutants or by transforming the bacterium with a DNA sequence which increases DMP activity.

To confer or otherwise impart a desirable property on a bacterium, as used herein, means to add, or to enhance a pre-existing property, e.g., nitrogen fixation, the ability to exert a plant growth promoting effect, an increased growth rate, the ability to repel pests, or any other property of a bacterium, which results in a desirable or beneficial effect on a plant, e.g., an agricultural plant.

A nifA gene product as used herein, refers to heterologous nifA gene product, i.e., a nifA gene product encoded by DNA derived from an organism of a species other than that of an organism into which DNA encoding the nifA gene product is derived, or more preferably to homologous nifA gene product, i.e., a nifA gene product encoded by DNA derived from an organism of the same species as that into which DNA encoding the nifA gene product is transformed.

The invention provides for the construction of bacterial strains transformed with the sequences that encode and express the dctA gene product, $C_4$-dicarboxylic acid membrane permease (DMP). Such strains possess an increased ability to take up $C_4$-dicarboxylic acids, substances which are found in plant root exudates, and which can be used as carbon sources by rhizospheric bacteria. The increased uptake of $C_4$-dicarboxylic acids leads to increased rhizospheric growth rates and thus to increased competitiveness. Some rhizospheric bacteria exert a beneficial effect for the plant (either naturally or because of a genetic modification), e.g., by affecting the plant, other rhizospheric bacteria, fungi, or nematodes, and the methods and materials of the invention can be used to increase the presence (e.g., in the rhizosphere or in the nodules of a host plant) of these desirable bacteria. For example, methods of the invention can be used to make biocidal strains of Pseudomonas, or nitrogen fixing strains of Rhizobium or Bradyrhizobium, more competitive.

The over-expression of dctA also results in an increase in nitrogen fixing capabilities, due to an increase in the provision of carbon from the plant to the nitrogen fixing bacteria.

DESCRIPTION OF PREFERRED EMBODIMENTS

FIG. 2 is the nucleotide sequence of dctA and the deduced amino acid sequence of the dctA gene product (Sequence I.D. No. 1).

FIG. 4 is a summary of the structure of the dct cassettes.

RHIZOSPHERIC BACTERIA WITH ENHANCED COMPETITIVENESS

Figures 1, 3:
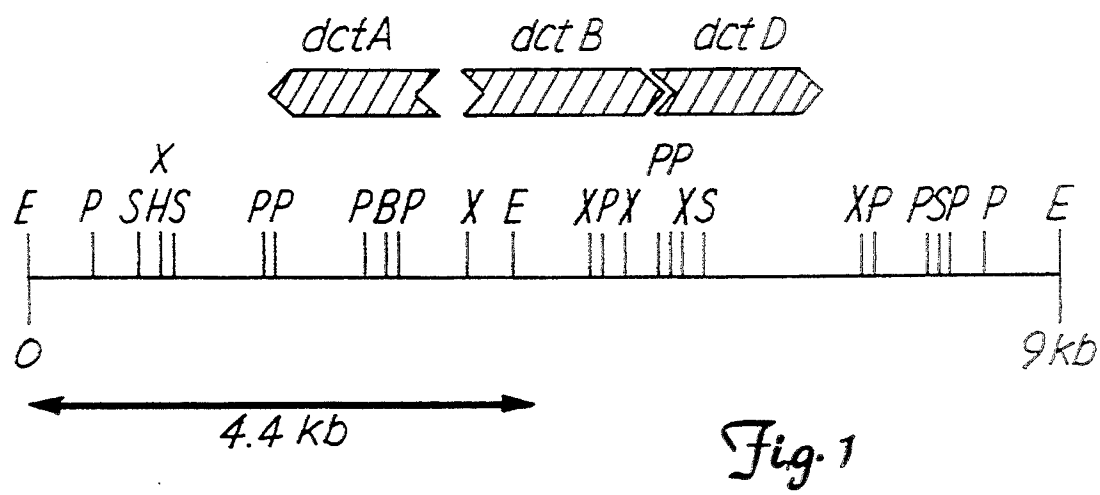
FIG. 1 is a map of the dct regulon.
FIG. 3 is a diagram of the structure of a transcriptional terminator downstream of the dctA gene (Sequence I.D. No. 2).

A rhizospheric bacterium must compete with other organisms in the rhizosphere. The competitiveness of a rhizospheric bacterium can be increased by increasing the growth rate of the bacterium, e.g., by increasing the ability of the bacterium to take up or metabolize some nutrient found in the rhizosphere.

$C_4$-dicarboxylic acids are a component of plant root exudates (and are thus present in the rhizosphere) and a large number of soil microbes can use dicarboxylic acids as a primary carbon source. In microbes, the uptake of the $C_4$-dicarboxylates, succinate, fumarate, and malate, is controlled by the genes, dctA, dctB, and dctD. The dctA gene encodes DMP which is responsible for the uptake of the carbon substrates. Expression of the dctA gene is sensitive to the presence of $C_4$-dicarboxylates in the environment and is controlled by a two component regulatory system encoded by the dctB and dctD genes. The dct genes from *Rhizobium leguminosarum* have been isolated and characterized (Ronson et al., (1987) *Nucl. Acids Res.* 15:7921–7934, hereby incorporated by reference; Ronson et al. (1984) J. Bact. 160:903–909, hereby incorporated by reference).

Microbial strains transformed with dctA are able to compete more effectively with parental strains, or native strains found in soil, in the rhizosphere. The increase in competitiveness is due to elevated levels of expression of DMP. Increased levels of DMP expression are achieved by transformation with the structural portion of dctA, under the control of its own or a heterologous promoter. One or more regulatory genes, e.g., dctB or dctD, may also be transformed into the strain.

dctA expressing Plasmids

The plasmids described herein are designed to elevate the cellular level of DMP in a microbial host into which they have been transformed. A plasmid containing the following components is useful in elevating the level of DMP in a host cell into which it is transformed: a dctA gene; a promoter to drive the transcription of the dctA gene; one or more selectable markers to simplify the selection of transformed organisms; and sequences capable of directing integration into a preferred chromosomal site. The choice of specific plasmid components, the arrangement and configuration of genes coding for selective markers and other components, the desirability of inclusion of an origin of replication capable of functioning in the microbial organism of choice, and other parameters, will be determined by factors known to those skilled in the art, e.g., by the intended recipient organism and chosen method of integration. Components of the vectors are discussed below.

dctA gene sequences: Coding sequences for any dctA gene or gene homologue can be used, providing that the presence of the gene within the host organism results in an increase in competitiveness, preferably by effecting an increase in dicarboxylic acid uptake by the host organism. To insure expression of the dct related genes and gene products, it is generally preferable to employ a homologous dct gene or portion thereof, i.e., a given host is transformed with a dct gene derived from that host, e.g., the *R. meliloti* gene in an *R. meliloti* host, or a Pseudomonas gene in a Pseudomonas host, when a homologous gene is available.

In the examples discussed below, dct genes from *Rhizobium leguminosarum* have been employed dct gene sequences from other species can be isolated by methods known to those skilled in the art. For example, in any microorganism capable of employing $C_4$-dicarboxylates as a primary carbon substrate, the genes responsible for $C_4$-dicarboxylate transport can be identified by mutagenesis, e.g., Tn5 mutagenesis, selection for mutants no longer capable of utilizing $C_4$-dicarboxylates as a principal carbon source, and screening of such mutants for the ability to transport succinate and/or malate. Once mutants are identified, the gene can be isolated using methods known to those skilled in the art.

See, e.g., Engelke et al., (1989) *J. Bact.* 171:5551-5560, hereby incorporated by reference; Ronson et al. (1984) supra.

Promoters: The dctA gene may be expressed from its own promoter or by fusion to another, heterologous, promoter. In the case of expression from its own promoter, it may also be desirable to include the dctB and dctD genes as part of the sequence to give increased expression of the dctA gene. The ability of a promoter to express a gene in a given environment can be determined by methods known to those skilled in the art, e.g., by fusing the lacZ gene to the gene under the control of the promoter, transforming the lacZ fusion into the organism of interest, and monitoring lacZ activity.

The promoter or promoters should express the gene or genes under their control during root colonization or during growth in the rhizosphere. In the case of nitrogen fixing or nodulating bacteria it is generally important that the promoter continue to function during infection of root hairs and nodulation.

Selectable markers: Transformation and integration into the genome are relatively rare events. Inclusion of DNA which encodes selectable marker proteins allows for the identification of transformants. A marker protein can be any protein which can be expressed in host cells and which enables the phenotypic identification of microorganisms which express the protein, e.g., proteins which confer resistance to one or more antibiotics, such as spectinomycin/streptomycin antibiotic resistance. (See, e.g., Prentki et al., (1984) Gene 29:303-313, hereby incorporated by reference.) Inclusion of a first marker on the backbone vector outside of the enhancement cassette, and a second marker, within the enhancement cassette, can be used to distinguish single vs. double cross-over integration, as is discussed below.

Termination signals: To prevent transcriptional read-through, the coding sequences present on the vector are followed by transcription termination signals at their 3' termini. Transcription termination signals are well known in the art and any functional signal is suitable for use in the plasmids of the invention. If more than one termination signal is present, different flanking termination signals should be used so as to avoid a recombination event within the cassette. In most embodiments, the native termination sequences accompanying the dctA gene can be used. Other useful termination signals include those associated with the Ω fragment (see below) and the T1T2 transcriptional terminators from the rrnB operon of *E. coli* (See Brosius et al., (1981) *J. Mol. Biol.* 148:107, hereby incorporated by reference; *Molecular Cloning: A Laboratory Manual,* eds. Maniatis, Fritsch and Sambrook, 1982, hereby incorporated by reference).

Enhancement cassette: All of the plasmid borne elements destined for integration into the host chromosome can be included in an enhancement cassette. Although preferred, this arrangement is not required, and those in the art will recognize other possible useful arrangements of the components involved. A cassette configuration is useful because it facilitates manipulations and alterations of the components of the cassette. The enhancement cassette can include (1) a promoter fused to a desired gene (or genes) involved in the expression of DMP, for example the dctA gene, the dct operon, or derivatives thereof; (2) a selectable marker gene for the selection of integrants carrying the cassette; (3) transcriptional and translational termination signals flanking or, in some cases, intervening between the above described genes to prevent transcriptional read-through from promoters in the adjacent chromosomal DNA and to prevent over-expression of chromosomal genes located downstream of the inserted cassette; and (4) flanking DNA sequences which are homologous to a region of the host genome, and which facilitate the integration of foreign DNA into the host chromosome by reciprocal homologous recombination.

Regions of Chromosomal Homology: There are many methods for achieving chromosomal integration known to the art, some of these require homologous recombination and some do not. The choice will depend on factors known to those skilled in the art, e.g., the host organism used. In embodiments where the integration is to be achieved by homologous recombination the sequences of the plasmid which are to be integrated into the host chromosome are flanked by regions which have homology to the host chromosome. Integration occurs as the result of recombination between the flanking sequences and homologous regions of the integration site on the host chromosome. The flanking regions should be of a size and of sufficient homology to the host DNA to permit integration, with the exact size most often being determined by the location of convenient restriction sites.

Generally, target integration sites are sites at which integration of DNA will have no detrimental effects on desirable or critical traits of the microorganism. Most often these will be regions of functionally silent DNA, known herein as neutral DNA. For the purpose of plasmid integration, neutral DNA need only to be silent with respect to traits required for desired biological activities of the organism, e.g., growth, nitrogen fixation, or pesticidal activity. Some functional sequences that are present in multiple copies within the genome maybe useful as sites for integration, particularly if disruption of one copy does not significantly alter the cellular levels of the encoded gene product or otherwise interfere with desirable traits of the host cell. In some instances it may even be desirable to integrate into functionally non-silent DNA, e.g., in the case where it is desirable to eliminate the expression of a normally expressed gene, such as a gene involved in inositol metabolism. Preferred integration sites for Rhizobium and Bradyrhizobium are the ino site (described below), the P3 site (described below), and the RSα9 site (described below). Similar sites in Pseudomonas include transposon insertion sites. Generally, intergenic regions provide useful integration sites in a variety of organisms.

Novel functionally silent DNA for chromosomal integration can be identified by methods known to those skilled in the art. For example, mutant host cells can be prepared by site-directed or random Tn5 mutagenesis e.g., as described below (See also e.g., Meade et al., (1981) *J. Bact.* 149:114-122, hereby incorporated by reference). The mutants generated can be screened for viability, bioactivity and other desirable traits by methods known to those skilled in the art. DNA, e.g., DNA bearing Tn5 insertions, can be cloned from the mutant strains with acceptable performance in regard to these or any other parameters which may be deemed important. DNA surrounding the cloned insertion can be used as target, i.e., integration site, DNA.

Origin of replication: The inclusion of origins of replication that are functional within the host organism may or may not be desirable, depending upon the organism and the intended method of integration. For example, in nitrogen-fixing bacteria, the preferred strategy for chromosomal integration of transformed plasmid DNA depends on whether the host is a fast growing species, e.g., Rhizobium, or a slow growing species, e.g., Bradyrhizobium. In fast growers, chromosomal integration is better accomplished by plasmid incompatibility techniques, i.e., where an origin of replication capable of functioning in the host strain is included on the transforming vector. Integration in slow growers is more efficient when suicide vector methodologies are employed. These techniques employ a vector which does not replicate within the host cell.

Host Microorganism

Any free living rhizosphere-colonizing bacterium which is capable of exerting a beneficial effect on a host plant can be tested, by methods known to those skilled in the art, to determine if the competitiveness of the bacterium can be increased by the methods and materials described herein.

Organisms commonly found in the rhizosphere include various species of the following genera: Rhizobium, Bradyrhizobium, Pseudomonas, Xanthomonas, Bacillus, Streptomyces, Serratia, and Enterobacter. Any microorganism can be screened for its ability to utilize $C_4$-dicarboxylates as a principal carbon source, by methods known to those skilled in the art. The ability to take up and metabolize C4-dicarboxylates may be improved for a species by increasing cellular DMP activity. This is most readily accomplished by increasing the number of dctA transcripts either through increased expression of endogenous genes or through the incorporation of additional expressible dctA genes. In general, organisms already possessing an endogenous dct system are preferred since their compatibility with $C_4$-dicarboxylate uptake is assured, and the addition of other accessory genes to produce a functional DMP may not be necessary.

Generally, it is preferred that the same bacterial species which naturally associates with the plant species be employed as the host species for a vector of the invention. For example, where the legume is alfalfa (*Medicago sativa*) and the aim is to improve nitrogen fixation, the modified host bacterium is preferably *R. meliloti;* where the legume is soybean (*Glycine max*), the bacterium is preferably *B. japonicum;* where the legume is the bean *Phaseolus vulgaris,* the bacterium is preferably *R. phaseoli;* and where the legume is clover, the bacterium is preferably *R. trifolii.*

Specific pairing of a plant with a bacterium which naturally associates with it is important for Rhizobia, but not for other species. Pairing is least important in embodiments where a biocidal property is being maximized.

Any Rhizobium or Bradyrhizobium strain is a suitable host, particularly one that is an effective nodulator. Many such strains are publicly available from the American Type Culture Collection (Rockville, Md.) or from the Rothamsted Collection of Rhizobium (Rothamsted Experimental Station, Harpenden, Hertfordshire, U.K.). In addition, the IBP World Catalogue of Rhizobium Collections (Allen et al., 1973, International Biological Programme, London) provides a listing of inocula available worldwide. Indigenous strains representing dominant species can be isolated from the field as by methods known to those skilled in the art, see e.g., Jenkins et al., (1985) *Soil Sci. Am. J.* 49:326, hereby incorporated by reference.

The host bacterium must be capable of colonizing the rhizosphere and exerting a beneficial effect on the plant-host. This includes bacteria which are able to grow in the rhizosphere, or which exert a beneficial effect, by virtue of a genetically engineered trait.

The competitiveness of a bacterial strain which has some other enhanced property, can be enhanced by the methods and/or materials described herein. For example, as described below, the competitiveness of Rhizobia expressing enhanced levels of the nifA gene can be enhanced by methods and materials described herein.

Transformation

Any of the numerous methods of transformation known to those skilled in the art may be used in the methods discussed herein, including e.g., chemical transformation, conjugation, phage transformation, or electroporation. In general, see Sambrook et al., *Experiments in Molecular Genetics,* Cold Spring Harbor Laboratory, hereby incorporated by reference; Balikrishnan et al., (1988) *Gene* 67:97–103, hereby incorporated by reference, Silhavy et al., *Experiments with Gene Fusions,* Cold Spring Harbor Laboratory, 1984, hereby incorporated by reference, and Barry (1986) *Bio/Technology* 4:446, hereby incorporated by reference. For an example of chemical transformation see Hanahan (1983) *J. Mol. Biol.* 166:557, hereby incorporated by reference. Electroporation has been described in many rhizospheric bacteria including Bacillus (Luchansky et al., (1988) *Molec. Microbiol.* 2:637, hereby incorporated by reference), and Bradyrhizobium (Guerinot et al. (1990) *Mol. Gen. Genetics* 221:287–290, hereby incorporated by reference).

Integration

In order to ensure that the constructs described above will be maintained in host cells, to avoid variation in plasmid retention and copy number, and to insure stability from strain to strain, it is beneficial to integrate the enhancing cassette into the chromosome of an appropriate host rather than maintain it as an extrachromosomal element. Vectors for the integration or insertion of dct gene fusions into the bacterial chromosome were constructed using an insertion vector that is able to direct insertion of DNA at a specific location within the bacterial genome. Site-specific insertion vectors have the advantage of allowing transfer of the cloned genes as part of the enhancement cassette to the bacterial host, and can also have the advantage of failing to incorporate the vector backbone into the chromosome. The preferred method for promoting integration depends on the microbial species utilized, e.g., some species may recombine easily with a given vector, whereas others may require specific combinations of genes or gene mutations. For example, either a "suicide vector" or an "incompatibility" approach may be used. The suicide vector approach can be used with *B. japonicum,* and involves the use of a vector having an origin of replication which is non-functional in the target cell. The transforming vector also contains a marker gene, e.g., an antibiotic resistance gene. As a result of the plasmid's failure to replicate, antibiotic resistant cells arise only by integration of the plasmid into the host chromosome. In the incompatibility approach, used with *R. meliloti,* the vector should include an origin of replication that is incompatible with another plasmid which is introduced into the transformed host, causing the loss of one of the plasmids. Integration of the dctA cassette and loss of the original plasmid can be identified by resistance or sensitivity to appropriate antibiotics, since antibiotic resistance genes are usually carried on each plasmid. The presence of different marker genes within the enhancement cassette and on the vector background allows further characterization of integrants as single or double crossover.

Integration may also be achieved by the use of a transposable element which bears the gene or genes of interest.

Competitiveness Testing

At various times it will be important to check the competitive ability of a newly engineered strain. For example, improved strains with higher levels of DMP activity may be compared to parental or other strains. It may also be important to compare performance of DMP over-expressing strains in differing environments. In such cases, the competitiveness of the DMP over-expressing strains may be evaluated either in the field or in the greenhouse. Competing strains may either be indigenous in the soil of choice, inoculated into sterilized soil, or a combination of indigenous and inoculum. Generally, the engineered strain and competing strain to be tested will be coinoculated into a soil, and a seed or germinating seed will be introduced. After a period of plant growth the microbial composition of the rhizosphere will be evaluated, either through the use of selective agents, reporter genes, microscopic analysis or other methods known to those skilled in the art, and the relative competitiveness determined.

Agricultural Applications

Once DMP over-expressing strains have been prepared, and their competitiveness ascertained, they may be employed in an agricultural situation. dctA enhanced strains will most often be used to provide a beneficial trait in the rhizosphere, e.g., pesticidal or nitrogen fixation activity. Delivery of these enhanced strains to the soil or rhizosphere, may be accomplished by traditional strategies in either liquid or solid inoculum form. Methods and references for formulations and their application are described by Paau (1988) *Trends in Bio/Technology* 6:276–279, incorporated herein by reference.

Application in liquid vehicles may occur via irrigation water and apparatus, through direct application with ground or aerial spraying apparati, by watering cans, or by any other appropriate method. Although application may be made as frequently as desired, in many cases just one application at the start of the growing season can be effective in insuring the persistence of dctA enhanced strains in the soil.

Application may also occur in the form of a coating on seeds or directly to the soil as a granular or powdered preparation. Seed coat preparations are currently preferred for the application of dctA engineered strains of rhizobia to legumes. Once applied, and, in the vicinity of planted seeds or growing plants, the cells will be free to divide and migrate, or be transported throughout the root zone.

Methods for the preparation of agricultural bacteria are known to those skilled in the art, see e.g., Paau (1986) European Patent Application 0203708, hereby incorporated by reference; Paau (1989) Applied and Environmental Microbiology 55:862–865, hereby incorporated by reference; Bellet et al. U.S. Pat. No. 4,161,397, hereby incorporated by reference; and Chao et al. (1984) Applied and Environmental Microbiology 47:94–97, hereby incorporated by reference.

EXAMPLE 1:

Strains and Vectors

Enhancement Cassettes

The dct enhancement cassettes used for transformation into *Rhizobium meliloti* and *Bradyrhizobium japonicum* contain engineered derivatives of the dct locus derived from *Rhizobium leguminosarum.* The Ω fragment described below, which confers resistance to spectinomycin and streptomycin, is also present in each of the cassettes.

The Ω fragment

The Ω fragment was obtained on plasmid pHP45Ω (Prentki et al., (1984), supra, and contains a gene, aadA, which confers resistance to streptomycin and spectinomycin. The aadA gene product results in the enzymatic adenylation of the antibiotic molecules, thereby abolishing their toxicity. The aadA sequences in pHP45Ω are bracketed with transcription and translation termination signals from bacteriophage T4, and restriction site polylinkers of known sequence. To facilitate the construction of the cassettes described below, the Ω fragment was subsequently altered either by sub-cloning into pUC19 (Yanisch-Perron et al., (1985) Gene 33:103–119, hereby incorporated by reference; also available from BRL, Gaithersburg, Md.) or by the addition of linkers.

The *Rhizobium leguminosarum* dct Locus

The Rhizobium transport system for $C_4$-dicarboxylates consists of a single protein permease, DMP, encoded by the dctA gene. The dctA-encoded permease transports succinate, fumarate, and malate. The expression of dctA is regulated by the dctB and dctD genes. The genetics of dicarboxylic acids transport in *Rhizobium leguminosarum* have been extensively studied (for a recent review, see Ronson, C. W. in *Nitrogen Fixation: A Hundred Years After,* H. Bothe, F. J. deBrujin and W. E. Nexton, eds. pp 547–551, hereby incorporated by reference). A genetic map of the *R. leguminosarum* dct region is shown in FIG. 1. In FIG. 1 dctA, dctB, and dctD, and their direction of transcription are shown as cross-hatched arrows; B=BamHI; H=HindIII; P=PstI; S=SalI; and X=XhoI. The dctB and dctD genes are regulatory genes which are required for $C_4$-dicarboxylic acid transport in free-living but not in symbiotic Rhizobia. The nucleotide sequence of the *R. leguminosarum* dctA gene, and the deduced sequence of its product, are shown in FIG. 2 (Sequence I.D. No. 1). The nucleotide sequence of the dctB and dctD genes has been published (Ronson et al., (1987) supra). Immediately downstream from the coding sequence of dctA is a structure characteristic of a rho-independent transcriptional terminator (see FIG. 2) which functions as a terminator.

The strains described below were engineered using DNA from the dct locus of *R. leguminosarum* as the starting material. This includes different subclones of the 6080 base pair region bordered by the HindIII site downstream of dctA and the PstI site downstream of dctD (See FIG. 1 and FIG. 4, which summarizes the structures of the dct cassettes).

Construction of dct Enhancement Cassettes

Four different versions of the dct region were constructed and integrated into the chromosome of *B. japonicum* or *R. meliloti* strains. The engineered dct genes fall into two classes: 1) genes that are expressed from their own promoters, and 2) gene fusions, wherein the gene in question has been fused to a promoter other than that from which it is normally expressed, as described below. The genes have been cloned into various vectors. In all cases the genes have been engineered as cassettes containing the Ω fragment (spectinomycin/-streptomycin resistance). Each of the cassettes has been transferred into the *B. japonicum* integration vector pMR19K (described below) for integration into the RSα9 site (described below) of Bj110 (described below), and into the *R. meliloti* integration vector pCR710 (described below) for integration into the P3 site (described below) of *R. meliloti* (described below).

The structures of the dct cassettes are summarized in FIG. 4. When the dctA gene has been fused to a heterologous promoter the full fusion is referred to e.g., as nptII promoter::dctA or Rm fixA promoter::dctA. The dct genes which are expressed from their own promoters are referred to by the dct gene only, without specification of the promoter, e.g., dctABD and dctA. FIG. 4A shows dctABD expressed from the dctA and dctB promoters, FIG. 4B shows dctA expressed from the dctA promoter, FIG. 4C shows dctA expressed from the nptII promoter, and FIG. 4D shows dctA expressed from Rm fixA promoter.

Figure 5:
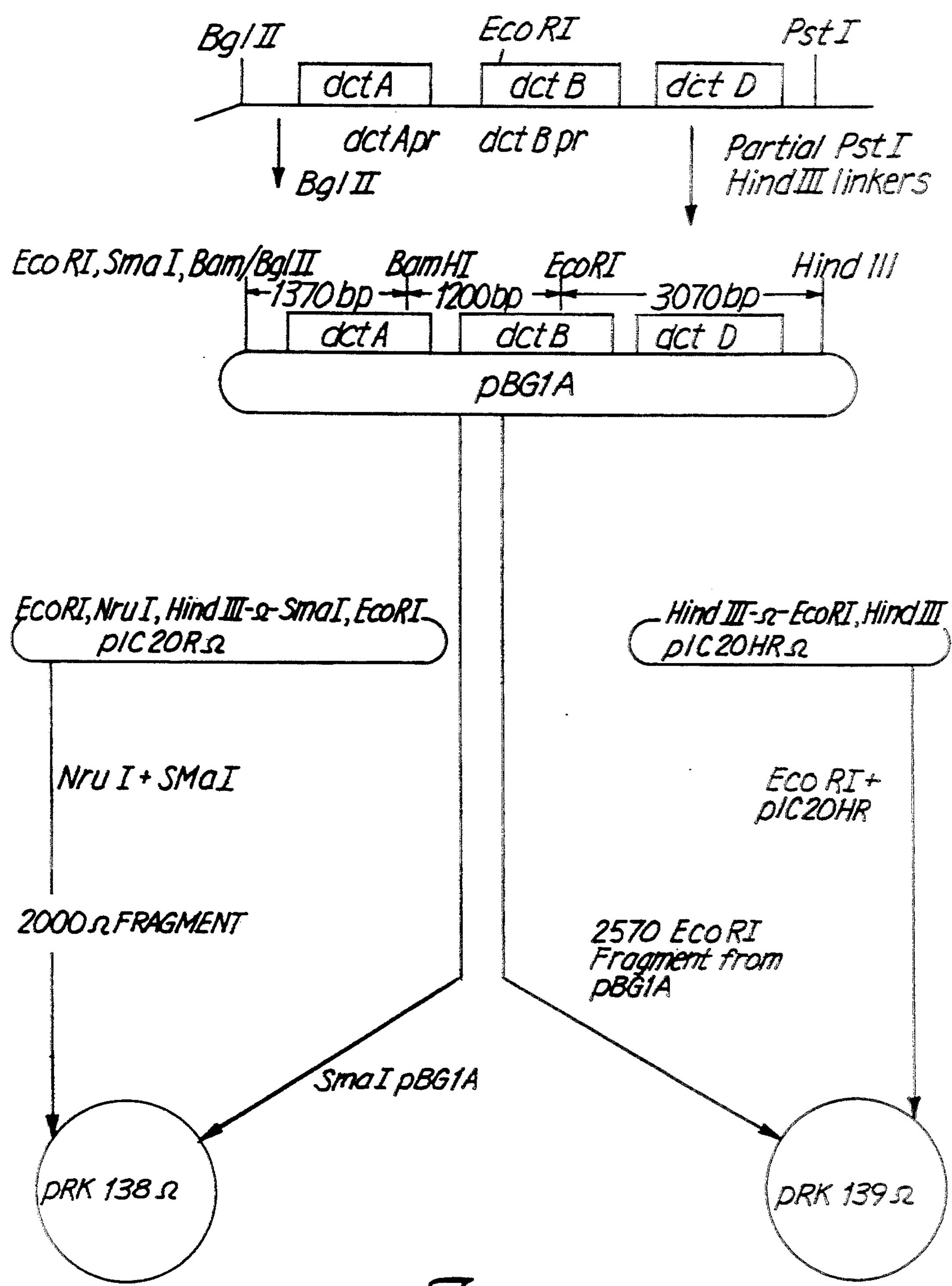
FIG. 5 is a diagram of the construction of pRK138Ω and pRK139Ω.

The dctABD and dctA Cassettes. The genes which are expressed from their normal promoters maintain the gene organization of the dct locus in *R. leguminosarum*. In that case the dctA gene is adjacent to, and transcribed divergently from, the dctB and dctD genes, which are expressed as an operon. Two derivatives of this locus were isolated and each of them fused with the Ω fragment. In one case all three genes (dctABD), and in the other only the transport gene (dctA), are expressed from their respective promoters. The construction of these strains involved a common intermediate and is outlined in FIG. 5.

Figure 6:
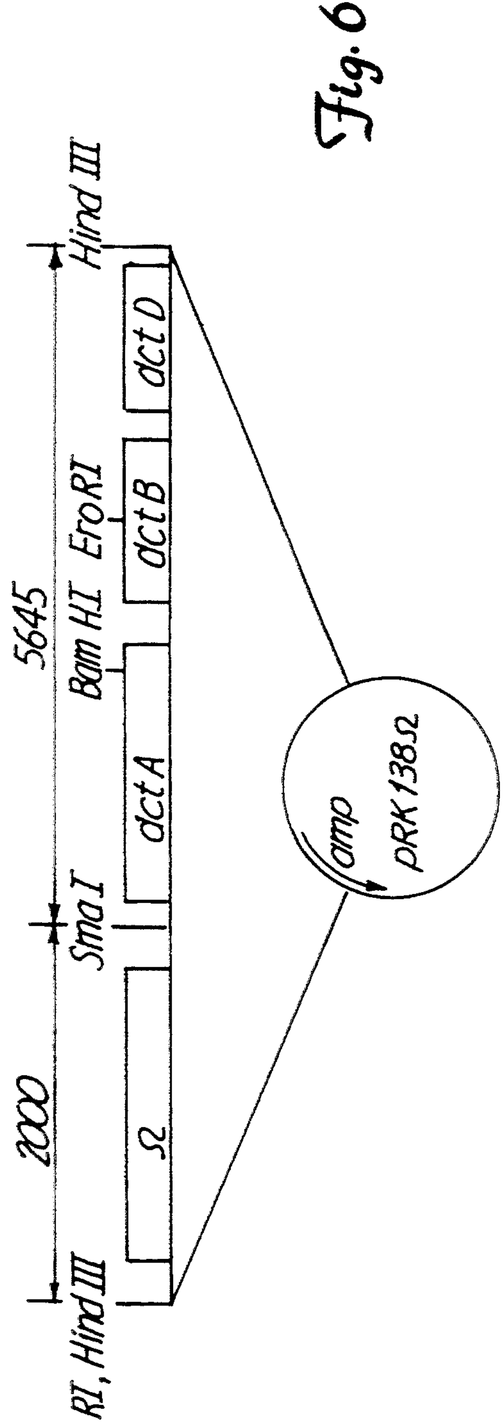
FIG. 6 is a diagram of pRK138Ω.

The dctABD/Ω Cassette. The dctABD/Ω cassette was assembled in the BamHI to HindIII sites of pUC13 (Yanisch-Perron (1985), supra) to form plasmid pRK138Ω, see FIG. 5. This includes the 5645 (the extra 5 bp are from the terminal restriction sites) base pair *R. leguminosarum* dct region from the BglII site downstream of dctA to the PstI site downstream of dctD. The PstI site was converted to a HindIII site by the use of linkers and the BglII site was ligated into the BamHI site (of pUC13) creating plasmid pBG1A. Thus, pBG1A is a 5640 bp BglII-PstI fragment of the *R. leguminosarum* chromosome inserted into the BamHI-HindIII sites of pUC13 (See FIG. 5). The 2000 base pair Ω fragment was isolated from pIC20RΩ (described below) on a NruI - SmaI fragment and blunt-end ligated into the SmaI site in pBG1A adjacent to the BamHI/BglII junction to yield pRK138Ω. pRK138Ω is a 7645 bp (2000 bp Ω region plus 5645 bp dct region) HindIII Ω::dctABD cassette in pUC13, as shown in FIG. 6. A HindIII site carried on the Ω fragment resulted in the creation of a HindIII cassette with the structure as shown in FIG. 6.

Figure 7:
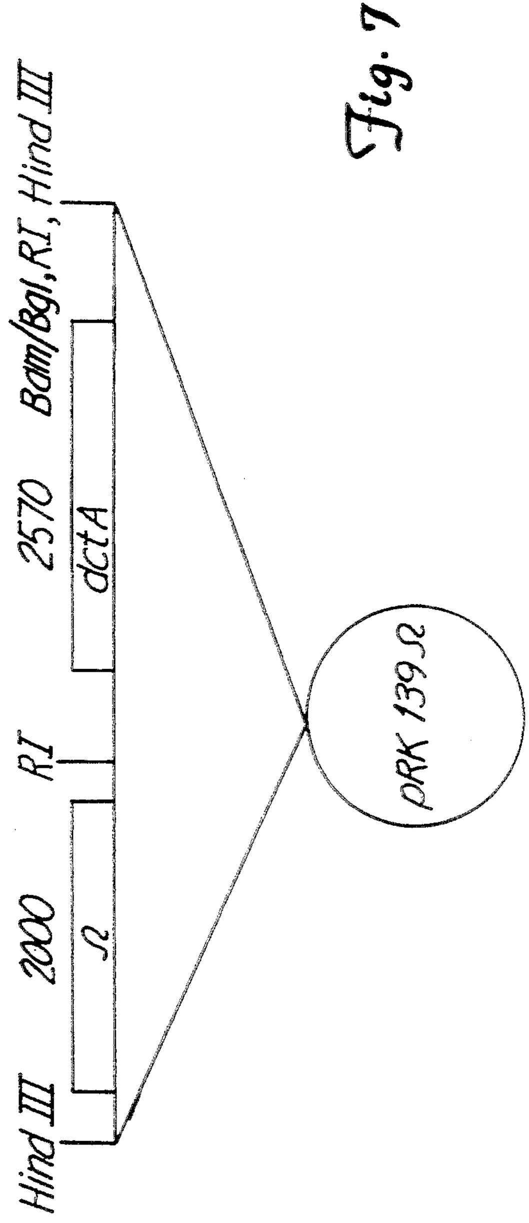
FIG. 7 is a diagram of pRK139Ω.

The dctA/Ω Cassette. The dctA/Ω cassette was assembled in pIC20H taking advantage of the HindIII sites bracketing the polylinker in pIC20H to create a HindIII cassette. The 2000 base pair Ω fragment was inserted into pIC20H (Marsh et al., (1984) *Gene* 32:481–485, hereby incorporated by reference) as a PstI fragment to form pIC20HΩ (See FIG. 5). The dctA gene and promoter was added to pIC20HΩ as a 2570 base pair EcoRI fragment isolated from pBG1A. This created pRK139Ω, which is a 4570 bp (2000 bp Ω plus 2570 bp dctA region) HindIII Ω::dctA cassette in pIC20H, as shown in FIG. 7.

The Promoter::dCtA Fusion Cassettes. Two fusions of the dctA gene to heterologous promoters have also been constructed. In these cases the dctA gene was engineered to create an NcoI or SphI site at the translation initiation site. The engineered dctA gene was then fused to promoters which had been similarly engineered therefore creating precise fusions at the translation initiation sites. Fusions have been constructed to the *R. meliloti* fixA promoter, which is an inducible promoter, and to the *E. coli* nptII promoter, which is a constitutive promoter. In both cases the dctA promoter, as well as the dctB promoter and dctBD coding regions, have been removed.

Figure 8:
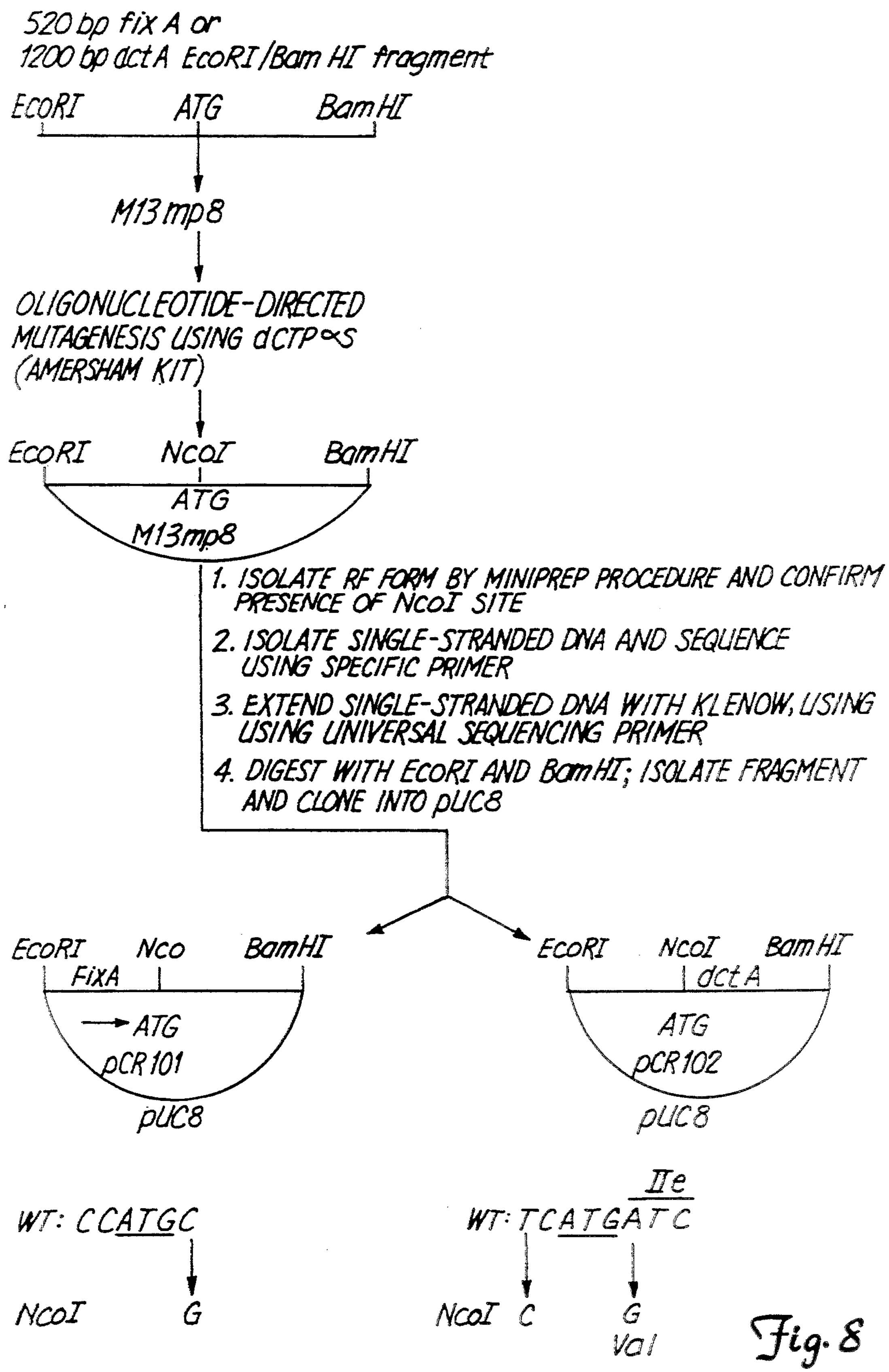
FIG. 8 is a description of the introduction of NcoI sites at the ATG initiation codons of fixA and dctA, using oligonucleotide-directed site-specific mutagenesis.

The Rm fixA promoter::dctA Fusion Cassette. In order to express the *R. leguminosarum* dctA gene from the *R. meliloti* fixA promoter while causing minimal disruption to promoter or dctA functions, the fusion was made at the +1 basepair of the translation initiation site of both DNA segments. This was achieved by creating an NcoI site (CCATGG) at the ATG initiation codons associated with dctA and also the fixA promoter, using oligonucleotide-directed site-specific mutagenesis as described in FIG. 8, by methods known to those skilled in the art. The NcoI site was then used to fuse the promoter sequence to the structural gene fragment. The source of the dctA gene was pCR26, which contains a 4.4 kb EcoRI fragment carrying dctA (See FIG. 1) purified from pPN104 (Ronson et al. (1984) supra) cloned into the vector pUC8 (Yanisch-Perron et al., (1985) supra; also available from BRL, Gaithersburg, Md.). The *R. meliloti* fixA promoter was purified from pCE201 (Earl et al. (1987), J. Bact. 169:1127–136, hereby incorporated by reference). A 1200bp EcoRI/BamHI fragment from pCR26 was cloned into M13mp8 for the site-specific mutagenesis of dctA, while a 520 bp EcoRI/BamHI fragment from pCE201 was used as the source for mutagenesis of the fixA promoter. The mutagenesis resulted in no change in the sequence of the fixA promoter, and in a change from A to G in the fourth base pair of the dctA coding sequence. This results in a conservative isoleucine-to-valine change in the amino acid sequence of dctA. The fixA promoter was then fused to the dctA structural gene, and the fusion gene ligated to the Ω element, as described in FIG. 9. The cloning resulted in a cassette that can be excised with HindIII. Note that the cassette is flanked by the Ω transcriptional terminators at one end and the dctA transcriptional terminators at the other end. Hence transcription originating in the cassette is contained within the cassette.

Figure 9:
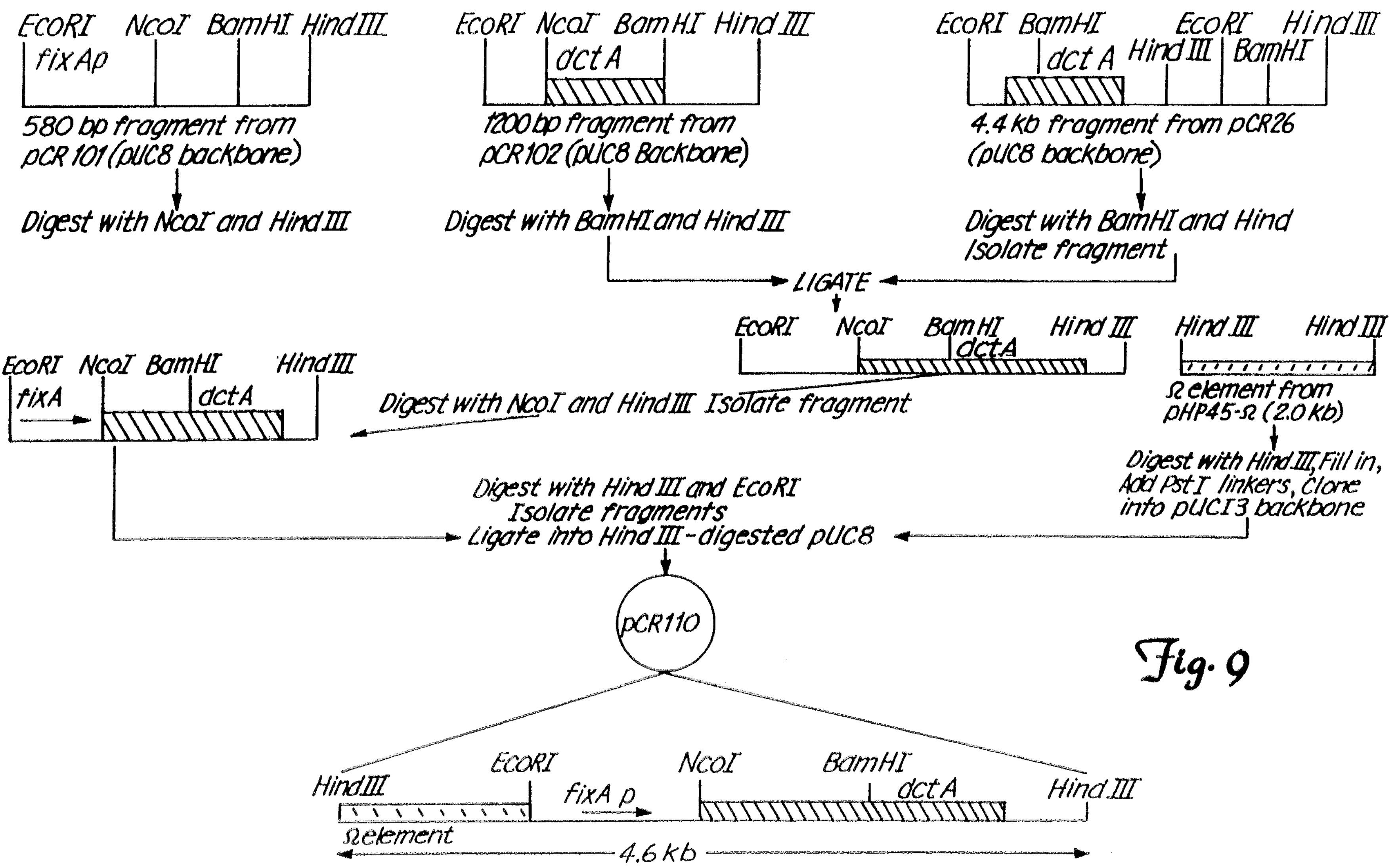
FIG. 9 is a diagram of the construction of the fixA promoter::dctA/Ω cassette.
Figures 10, 12:
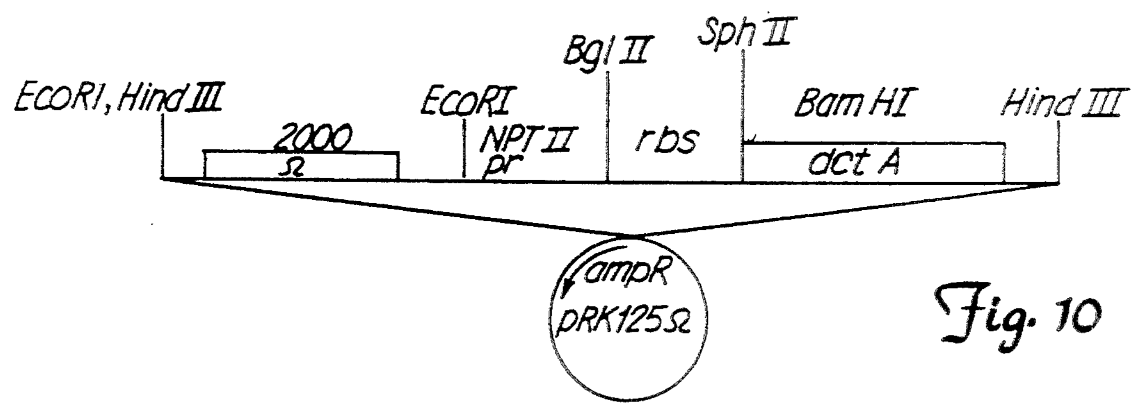
FIG. 10 is a map of pRK125Ω.
FIG. 12 is a sequence of a synthetic oligonucleotide carrying the ribosome binding site used on the nptII promoter dctA fusion (Sequence I.D. No. 3).
Figure 11:
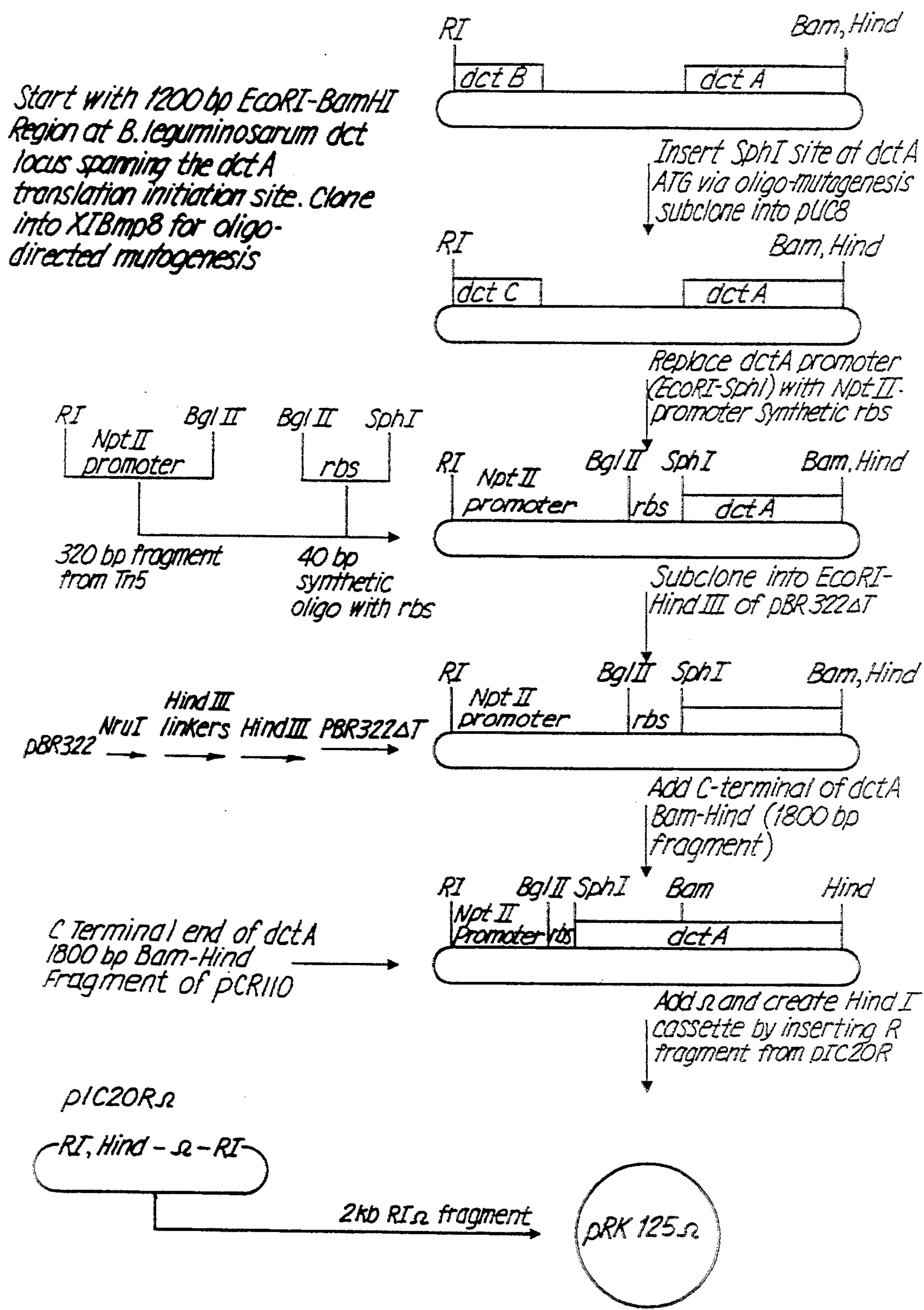
FIG. 11 is a flow chart summarizing the construction of pRK125Ω.

The nptII promoter::dctA Fusion Cassette. The nptII promoter::dctA::Ω cassette was assembled in pBR322ΔT to form pRK125Ω, shown in FIG. 10. pBR322ΔT is pBR322 with the HindIII to NruI region containing the tetracycline resistance gene deleted. Plasmid pBR322ΔT was created by cutting with NruI, adding HindIII linkers, cutting with HindIII and religating, therefore deleting the tet gene. A flow chart outlining the assembly of pRR125Ω is shown in FIG. 11. The same 1200 base pair EcoRI to BamHI fragment used to create the Rm fixApr::dctA fusion described above was cloned into M13mp8 for oligo-nucleotide mutagenesis (Amersham). The procedure is the same as that summarized in FIG. 8 except that an SphI site instead of an NcoI site was inserted at the translation start. This resulted in the DNA sequence being changed from TCATGATC to GCATGCTC which created the SphI site and changed the second amino acid from isoleucine to leucine. After subcloning the mutagenized fragment into pUC8, the HindIII to SphI region carrying the dctA promoter was deleted and replaced by two fragments which include the 320 base pair HindIII to BglII region of Tn5 (which carries the nptII promoter) plus a 40 base pair synthetic oligonucleotide (which carries a ribosome binding site (rbs) flanked by BglII and SphI sites). The sequence of the synthetic rbs is shown in FIG. 12 (Sequence I.D. No. 3). The EcoRI to HindIII fragment carrying the nptII promoter::synthetic rbs::dctA fusion was then sub-cloned into pBR322ΔT to facilitate subsequent manipulations. The C-terminal end of dctA was added on an 1800 base pair BamHI to HindIII fragment isolated from pCR110 (the structure of pCR110 is shown in FIG. 9) so that an nptII promoter::synthetic rbs::dctA fusion was created in pBR322ΔT. The 2000 base pair Ω fragment was obtained as an EcoRI fragment from pIC20RΩ and inserted upstream of the nptII promoter thereby creating the final HindIII cassette and forming plasmid pRK125Ω (FIG. 10).

Integration

The cassettes described above were transferred to *B. japonicum* and *R. meliloti* integration vectors for integration into the host chromosome. Integration into the *B. japonicum* genome was accomplished using a suicide vector approach and integration into the *R. meliloti* chromosome utilized plasmid incompatibility.

Integration: *Bradyrhizobium japonicum*

Host strains BJB1000 and BJB2000. BJB1000 is strain identification number for strain USDA 1-110. Strain USDA 110 is a commercial inoculant strain (e.g., Nitragin strain 61A89), and has been the subject of extensive ecological and genetic studies over several years in many laboratories. *Bradyrhizobium japonicum* strain USDA 1-110 was derived from strain USDA 110, by methods known to those skilled in the art, as a variant that was unable to utilize mannitol but that was efficient in symbiotic nitrogen fixation. Strain USDA 1-110 is not a mutant of USDA 110; rather it seems that strain USDA 110 is a heterogeneous collection of colony types, and that I-110 is a naturally occurring isolate that is typical of one of these colony types. DNA from strain I-110 shows identical restriction endonuclease patterns to that from strain USDA 110, and neither strain contains detectable indigenous plasmids. Both USDA 110 and USDA I-110 are listed in the Beltsville Rhizobium Culture Collection Catalog published by the USDA Agriculture Research Service, hereby incorporated by reference, and can be obtained from the Beltsville Culture Collection. According to the Beltsville Rhizobium Culture Catalog, strain USDA 110 was originally isolated in Florida in 1959.

*Bradyrhizobium japonicum* strain BJB2000 was isolated in 1987 by BioTechnica International, Inc. from a soybean nodule harvested from the Chippewa Agricultural Station in Pepin County, Wis. (CASI). Strains isolated and characterized from six other randomly selected nodules from CASI-grown plants were indistinguishable from BJB2000, indicating that BJB2000 was the dominant *B. japonicum* strain in this location in 1987. BJB2000 belongs to serogroup 110 (H. Keyser, USDA, personal communication). BJB2000 is similar to BJB1000 in several ways. The two strains cannot be differentiated from one another on the basis of their DNA restriction enzyme digestion patterns, and are extremely similar in their intrinsic resistances to the 45 antibiotics tested. Furthermore, the hybridization patterns obtained with BJB1000 and BJB2000 DNA are similar, using a labelled 13.5 kb DNA fragment containing the nifDK operon as a probe.

Figure 13:
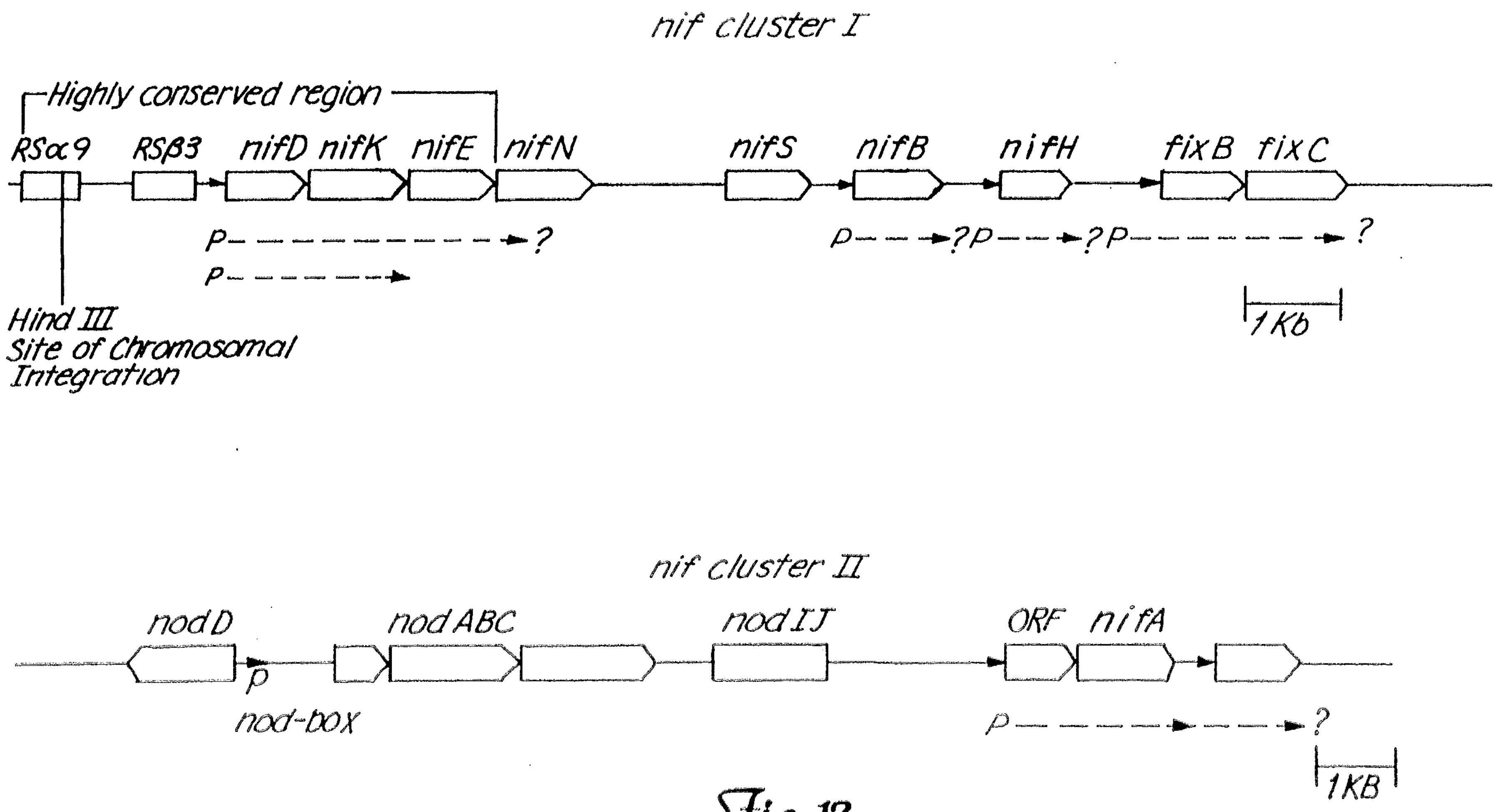
FIG. 13 is a map of *B. japonicum* nif clusters I and II.
Figure 14:
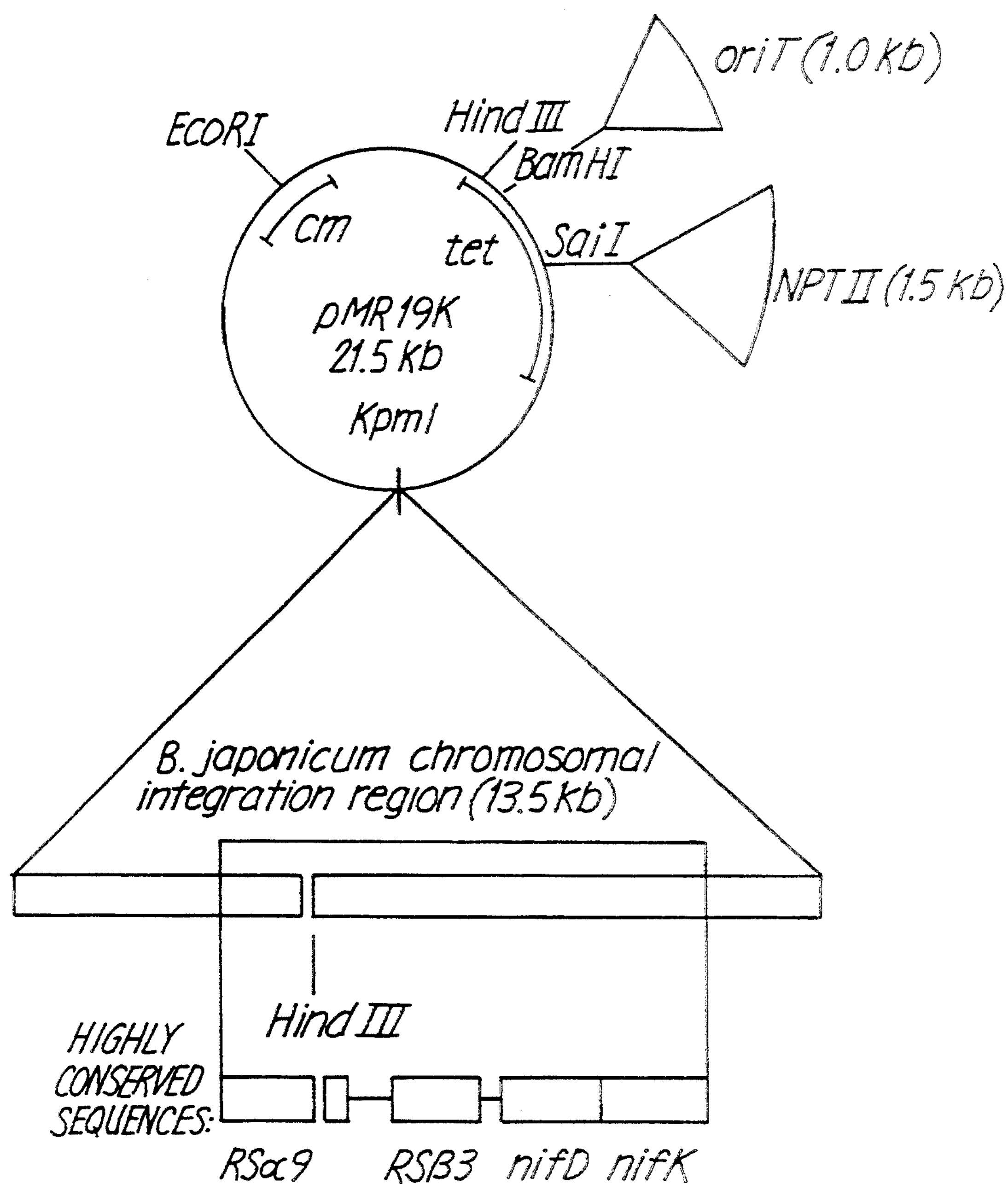
FIG. 14 is a map of pMR19K.

The Chromosomal Integration Site. A well-characterized region of the *B. japonicum* chromosome was chosen as the site for the insertion of desired genes. This chromosomal region is contained within a 13.5 kb KpnI fragment which includes the nifDK operon (Hennecke et al. (1987) in, *Molecular Genetics of Plant-Microbe Interactions,* Verma and Brisson, eds., hereby incorporated by reference). The fragment was first isolated and studied as a part of nif cluster I (FIG. 13), and except for integration into the essential nifDK operon, Tn5 mutations in this region produce Fix+ phenotypes, Noti et al., (1986) *J. Bact.* 167:774–783, hereby incorporated by reference, and Yun et al. (1986) *J. Bact.* 167:784–791, hereby incorporated by reference. Legocki et al., (1986) *Proc. Natl. Acad. Sci. USA* 83:9080–9084, hereby incorporated by reference, and Yun et al., (1986) supra, have also used the 13.5 kb fragment as the integration region for delivery of exogenous DNA. In FIG. 13, dotted lines indicate transcripts initiated from identified promoters (p). Question marks at the end of transcripts indicate that the transcription termination sites are not known.

*Bradyrhizobium japonicum* strain I-110 (BJB1000) contains several different repeated sequences, termed RSα (12 copies), RSβ (6 copies), RSγ (12 copies), RSδ (10 copies), and RSε (4 copies). Several of these repeated sequences are located near nil cluster I (Hahn et al., (1987a) *Appl. Env. Micro.* 53:2247–2252, hereby incorporated by reference; Kaluza et al. (1985) *J. Bact.* 162:535–542, hereby incorporated by reference). There is a HindIII site within one of these repeat sequences, RSα9, which is within nif cluster I (Kaluza et al., (1985) supra). This site was chosen for the insertion of desired genes into the chromosome (FIG. 13). RSα9 and two other RSα species were sequenced and found to be nearly identical (Kaluza et al., (1985) supra). RSα9 contains two open reading frames (ORFs) that are disrupted by insertion at the HindIII site, but these ORFs have not been shown to encode any functional proteins. Tn5 insertions in the region around this HindIII site have been shown to have a symbiotically silent (Fix+) phenotype (Kaluza et al., (1985) supra; Noti et al., (1986) supra). Despite the presence of repeated sequences, nif cluster I appears to be very stable (Hahn et al., (1987a) supra; Hahn et al., (1987b) Appl. Env. Micro. 53:2253–2255; Kaluza et al., (1985) supra). Deletion mutants in nif cluster I can be isolated under laboratory conditions, and some of these may arise from recombinations between repeat sequences (Hahn et al., (1987b) supra). However, a study of 80 derivatives of strain USDA 110 revealed no changes in the pattern of RS hybridization (Hahn et al., (1987b) supra) and a study of several different *B. japonicum* strains showed that nif cluster I, including RSα9, is highly conserved in most strains. On the other hand, changes in the distribution of the RS sequences located outside nif cluster I were readily detected in all strains (Hahn et al., (1987b) supra). Integrations into a site between RSα9 and RSβ3, have been shown to be stable (Acuna et al., (1987) *Plant Mol. Biol.* 9:41–50, hereby incorporated by reference).

Although recombination between flanking repeat sequences might lead to the loss of the integrated and flanking DNA, such events are extremely rare in wild-type *B. japonicum* and do not occur at a measurable frequency in the integrated strains (Acuna et al., (1987) supra). Although RS sequences have some characteristics of insertion sequences (Kaluza et al., (1985) supra), transposition of RS sequences has never been observed (Hahn et al., (1987a) supra; Kaluza et al., (1985) supra), and there is no DNA sequence homology with any transposase genes. The genomic positions of the RS sequences in nif cluster I have been conserved through many generations of several 110 derivatives and in related strains. This suggests that this region is genetically stable.

Integration Vectors. The integration vector used has the following features: (a) a 13.5 kb fragment of a conserved region from the *B. japonicum* I-110 chromosome which contains a unique HindIII site for insertion of desired genes (allowing the creation of a sequence including inserted genes flanked by contiguous regions of *B. japonicum* DNA; (b) sequences encoding genes for selectable antibiotic resistances; (c) an oriT sequence, to allow the vector to be mobilized into *B. japonicum* in a triparental cross; (d) an origin of replication (oriV), which is functional only in *E. coli* and not *B. japonicum*, so that the vector is unable to replicate in *B. japonicum*. When mobilized into *B. japonicum* by conjugation, the DNA inserted in the HindIII site is integrated into the chromosome through a double recombination event between the flanking regions of homology on the plasmid and their native locus on the *B. japonicum* chromosome.

Figure 15:
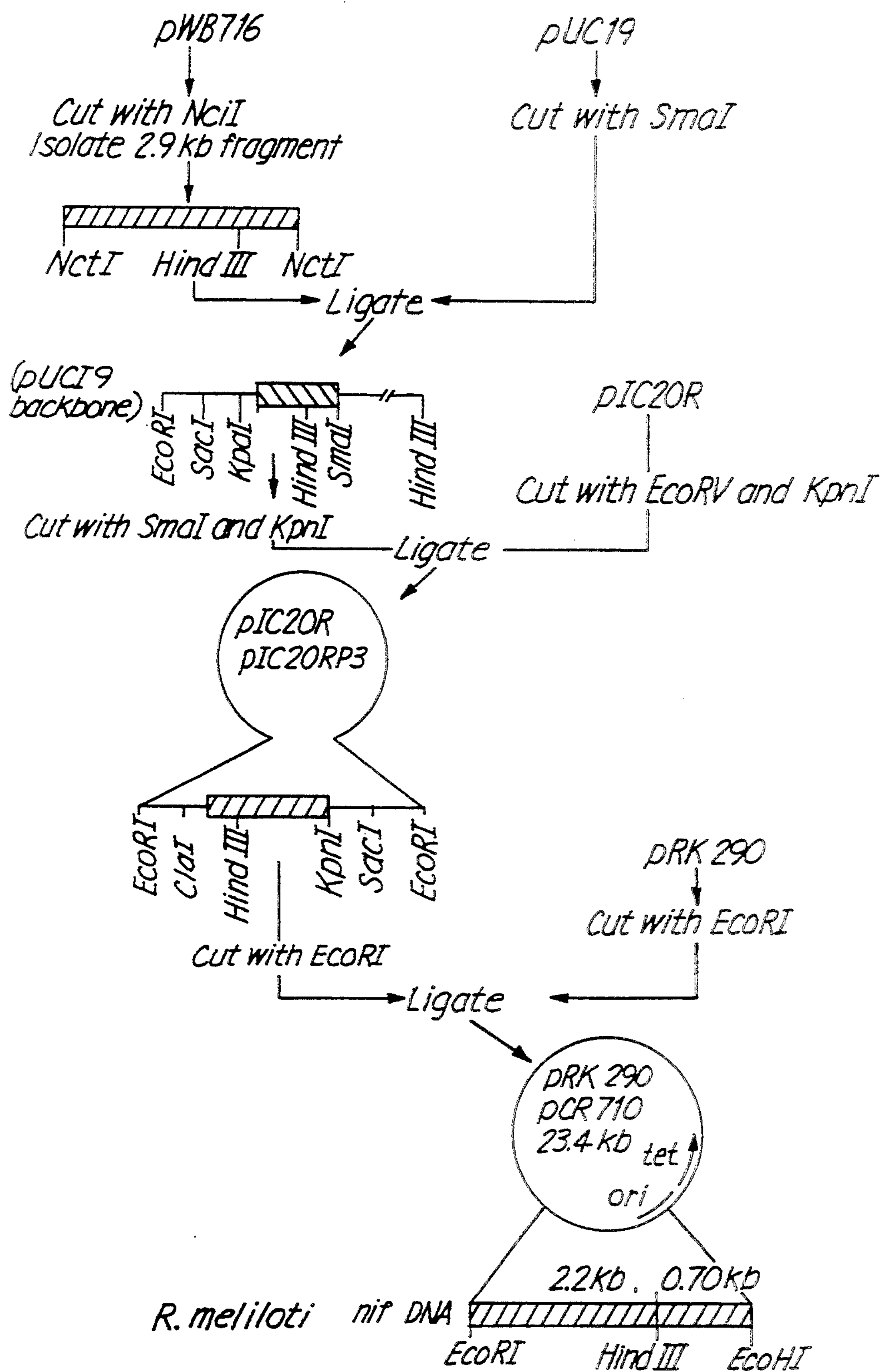
FIG. 15 is a summary of the construction of pCR710.

The integration vector used in the work described herein was derived from pMR19 of Legocki et al., (1986) supra, which was in turn derived from pJN13 of Yun et al., (1986) supra. Plasmid pJN13 contains a 13.5 kb KpnI fragment of the *B.* japonicum I-110 chromosome cloned into the PstI site of pBR325 and the RP4 oriT locus cloned into the EcoRI site of pBR325. These insertions disrupt the ampicillin resistance gene and chloramphenicol resistance gene, respectively. Legocki et al., (1986) supra modified pJN13 by moving the oriT sequence from the EcoRI site to the BamHI site, restoring the chloramphenicol resistance gene at the EcoRI site to yield pMR19. Since the BamHI site is within the tetracycline resistance gene, this makes pMR19 tetracycline sensitive ($Tc^s$) and chloramphenicol resistant ($Cm^4$).

pMR19 was modified by the insertion of the Tn5 nptII (kanamycin resistance $Km^r$) gene, excised from Tn5 as a HindIII-SalI fragment, into the SalI site. The resultant vector, pMR19K, is $Tc^s$, $Km^r$ and $Cm^r$ and is shown in FIG. 15.

Transformation and Analyses of recombinant strains

The enhancement cassettes containing the engineered dct genes plus the Ω marker were inserted into the unique HindIII site of pMR19K. The plasmid containing the enhancement cassette was introduced into the host strain via tri-parental mating using pRK2013 as the helper strain (Figurski, et al. (1979), *Proc. Natl. Acad. Sci. USA* 76:1648–1652, hereby incorporated by reference) and rifampicin (5 μg/ml) as a counterselection. Positive growth on Rhizobium defined medium (RDM, RDM contains the following: Potassium gluconate, 5.0 g/l; $K_2HPO_4$, 0.22 g/l; $MgSO_4 \cdot 7H_2O$, 0.1 g/l; Sodium glutamate, 1.1 g/l; 1000× trace elements, 1.0 ml/l; 1000× vitamin stock, 1.0 ml/l; and Agar, 20. g/l. 1000× vitamin stock solution contains: riboflavin, p-amino benzoic acid, nicotinic acid, biotin, thiamine-HCl, pyridoxine-HCl, and calcium pantothenate, all at 4.0 mg/l; and myo-inositol, 24.0 mg/l. The 1000× vitamin stock should be filter sterilized. The 1000× trace elements stock solution contains, per 200 ml: $CaCl_2$, 1.0 g; $H_3BO_3$, 29.0 mg; $FeSO_4 \cdot 7H_2O$, 25.0 mg; $COSO_4 \cdot 7H_2O$, 14.0 mg; $CuSO_4 \cdot 7H_2O$, 1.0 mg; $MnCl_2 \cdot 4H_2O$, 0.86 mg; $ZnSO_4 \cdot 7H_2O$, 21.6 mg; $Na_2MoO_4$, 25.0 mg; and nitrilo-triacetate, 1.4 g. The 1000× trace element solution is adjusted to pH 5.0.) containing streptomycin (200 μg/ml) and spectinomycin (1000 μg/ml), due to the presence of the Ω marker, and sensitivity to kanamycin (200 μg/ml) specified by the vector moiety of the construction (pMR19K) indicated that a stable, double cross-over event had occurred after conjugation. A single cross-over event, resulting in gene duplication, results in an Ω resistance/vector-resistance phenotype. The structure of the integrated genes was confirmed by Southern blot hybridization.

Integration: *Rhizobium meliloti*

Host Strains RCR2011 (SU47) and PC. *R. meliloti* strain RCR2011, also known as SU47, is a natural isolate, obtained from and available from the Rothamsted Experimental Station Collection.

PC is a natural strain isolated by BioTechnica International in 1986 from Pepin County, Wis. It has similar nitrogen-fixing ability to that of RCR2011 but is much more competitive.

Integration Site. The integration site used to introduce the dct enhancement cassettes was the HindIII site located within the "P3" region between the nifHDK and fixABCX operons of the nif cluster on megaplasmid pRmSU47a (Better et al. (1983) Cell 35:479–485, hereby incorporated by reference; Finan et al., (1986) *J. Bact.* 167:66–72, hereby incorporated by reference; Earl et al. (1987) supra). This site was chosen because it is within a well-characterized region of the genome, and because transposon insertions within the P3 region have no effects on the symbiotic properties of *R. meliloti.* The P3 region has been extensively characterized by Better et al., (1983) *Cell* 35:479–485, hereby incorporated by reference. Earlier studies had shown by transposon Tn5 mutagenesis that the region between the nifHDK and fixABCX operons was symbiotically silent (Ruvkun et al., (1982) Cell 29:551–559, hereby incorporated by reference; Corbin et al., (1982) *J. Bacteriol.* 149:221–228, hereby incorporated by reference, and Corbin et al. (1983) *Proc. Natl. Acad. Sci. USA* 80:3005–3009, hereby incorporated by reference). Better et al., (1983), supra, showed by hybridization studies that the region contained sequences similar to the nifHDK and fixABCX promoters and termed the region "P3". DNA sequence analysis revealed a region of extensive homology to these promoters, see Better et al. (1983), supra. In particular, the P3 promoter was strongly conserved with the nifHDK promoter from about 170 bp before the transcriptional initiation point to 47 bp downstream of the translational initiation site, including the 80 bp leader RNA sequence. The homology with nifH coding sequence abruptly ends after 47 bp and the P3 open reading frame is only 69 bp long, with a coding capacity for 23 amino acids. The P3 promoter is transcribed in nodules (Corbin et al., (1982), supra; Corbin et al., (1983), supra, but there is no evidence that the RNA is translated and no protein products have been detected from the region. This led Better et al., (1983), supra, to propose that "P3" is a "vestigial" promoter which arose as a chromosomal duplication of the nifH promoter and the first 47 bp of the nifH gene. This duplication has been conserved among several strains of *R. meliloti* (Better et al., (1983), supra). The HindIII site within the P3 region occurs 53 bp upstream of the site of initiation of P3 RNA. Hence insertions at the HindIII site may disrupt the P3 promoter but do not disrupt any coding sequence.

Integration Vector. The construction of the P3 site integration vector, pCR710, is outlined in FIG. 15. The P3 region and flanking DNA were isolated as a 2.9 kb NciI fragment from cosmid pWB716 (Buikema et al., (1983) *J. Molec. Appl. Genet.* 2:249–260, hereby incorporated by reference) which covers the nif region. The identity of the fragment was confirmed by digesting the isolated fragment separately with XhoI, HindIII and EcoRI. In each case, fragments of the appropriate size predicted from available nucleotide sequence were obtained. Most of the sequence of the nif region has been published, except for about 900 bp between the nifH promoter to within 220 bp of the HindIII site in P3 (Better et al., (1983), supra; Earl et al. (1983), supra). The isolated 2.9 kb NciI fragment was blunt-end ligated into the SmaI site of vector pUC19 (Yanisch-Peron et al., (1985) supra). This recreated a SmaI site at one end of the fragment and enabled the fragment to be excised as a SmaI KpnI fragment and cloned into vector pIC-2OR (Marsh et al., (1984) supra) cut with EcoRI and KpnI to yield plasmid pIC20RP3. The fragment was then excised with EcoRI and cloned into the unique EcoRI site of pRK290 (Ditta et al., (1980) *Proc. Natl. Acad. Sci. USA* 77:7347–7351, hereby incorporated by reference), giving pCR710. The integration vector pCR710 contains a unique HindIII site for incorporation of genes for subsequent integration into the P3 region of the *R. meliloti* genome.

Integration Procedure and Analysis of the Recombinant Strains. The enhancement cassettes containing the dct engineered derivatives and the Ω marker were transferred to the HindIII site of pCR710 and subsequently integrated into the P3 site of the genome using a two-step incompatibility approach. The pCR710 derivative was conjugated into the host strain by tri-parental mating using pRK2013 as the helper plasmid (Figurski et al., (1979) supra) and cinoxacin (20 μg/ml) as a counterselection. The plasmid was selected for by resistance to tetracycline (5 μg/ml) coded on the pRK290 backbone of pCR710 and streptomycin (100 μg/ml) plus spectinomycin (100 μg/ml) due to the Ω portion of the enhancement cassette. Incompatible plasmid pJB251, which is a spectinomycin-sensitive derivative of pPH1J1 (Hirsch et al., (1984) *Plasmid* 12:139–141, hereby incorporated by reference) and which confers resistance to gentamycin (40 μg/ml), was then crossed into the *R. meliloti* strain carrying the plasmid-borne dct enhancement cassette. The exconjugants from this cross were selected for resistance to gentamycin, spectinomycin and streptomycin. Plasmids pJB251 and the pCR710 derivatives are incompatible since both carry a P-group origin of replication. Therefore selection for gentamycin, spectinomycin, and streptomycin resistance plus sensitivity to tetracycine allowed identification of the strains which have the enhancement cassette integrated into the P3 site by homologous recombination and that have lost the pCR710 replicon. The pJB251 plasmid was cured by inoculating the resultant strains onto alfalfa and screening bacteria isolated from nodules for sensitivity to gentamycin. The structure of the recombinant strains was confirmed by Southern blot hybridization analysis.

EXAMPLE 2

*B. japonicum* Rhizosphere Establishment

A strain of *Bradyrhizobium japonicum* (BJB1003) containing an additional copy of the dctA gene expressed from the *R. meliloti* fixA promoter (BJB1003 has an RmfixApr::dctA::Ω cassette integrated at the RSα9 site of I-110) was tested for its ability to competitively colonize the rhizosphere of soybeans. Field tests were conducted in 1989 at Louisiana State University, Baton Rouge, La.

Approximately 14 days before beginning the tests, the site of the plots were treated with herbicide to control weeds. Soybeans were sown (8–10 per foot) in rows 3 feet apart at a depth of approximately 1.0 to 1.5 inches. The sowing equipment was thoroughly cleansed after the application of all the replicates of one treatment by rinsing with 50% ethanol followed by water.

*Bradyrhizobium japonicum* were grown in shaker flasks to a density of $10^9$ cells/ml or greater. Cells were then pelleted, washed twice with distilled water and then re-suspended in an equal volume of distilled water. The cells were added to finely ground vermiculite carrier at a rate of 1.5ml of suspension to 1 gram of carrier. The inoculum was stored in this form in a sterile centrifuge bottle for two weeks. The vermiculite carrier was coated onto the seeds within two hours of planting by adding 0.65gm of the inoculated vermiculite to 50 gm of seed in a Whirl-Pac bag. The bag containing the inoculated vermiculite plus seeds was sealed and shaken vigorously until the seeds were evenly coated. This treatment lead to an inoculation rate of between $10^5$ and $10^6$ bacteria per seed.

Microbial colonization of the rhizosphere was tested by periodically sampling the inner rhizosphere of specific plants. Aggregated outer rhizosphere soil was removed by vigorous shaking. The root system of each plant was then transferred to a separate container containing 3 g of glass beads and sufficient volume of 0.1% Tween 80 to immerse the entire root. The root system underwent a vigorous wash for 30 minutes on a wrist-action shaker. Serial dilution series from each root wash were spread-plated onto selective and non-selective media. The selective medium contained spectinomycin (1000 μg/ml) and streptomycin (200 μg/ml) as well as the fungistats cyclohexamide (75 μg/ml) and nystatin (75 μg/ml). The genetically-engineered strains were identified as $Spc^r/Sm^r$ due to the presence of the Ω fragment. The non-selective medium was RDM containing the fungistats cyclohexamide (75 μg/ml) and nystatin (75 μg/ml). The wash was then transferred to a tared plastic weigh boat and dried to assess dry weight of the inner rhizosphere soil sample. The washed root system was dried briefly with paper toweling and weighed to determine root fresh weight. The sample was then be dried to assess root dry weight.

Figure 16:
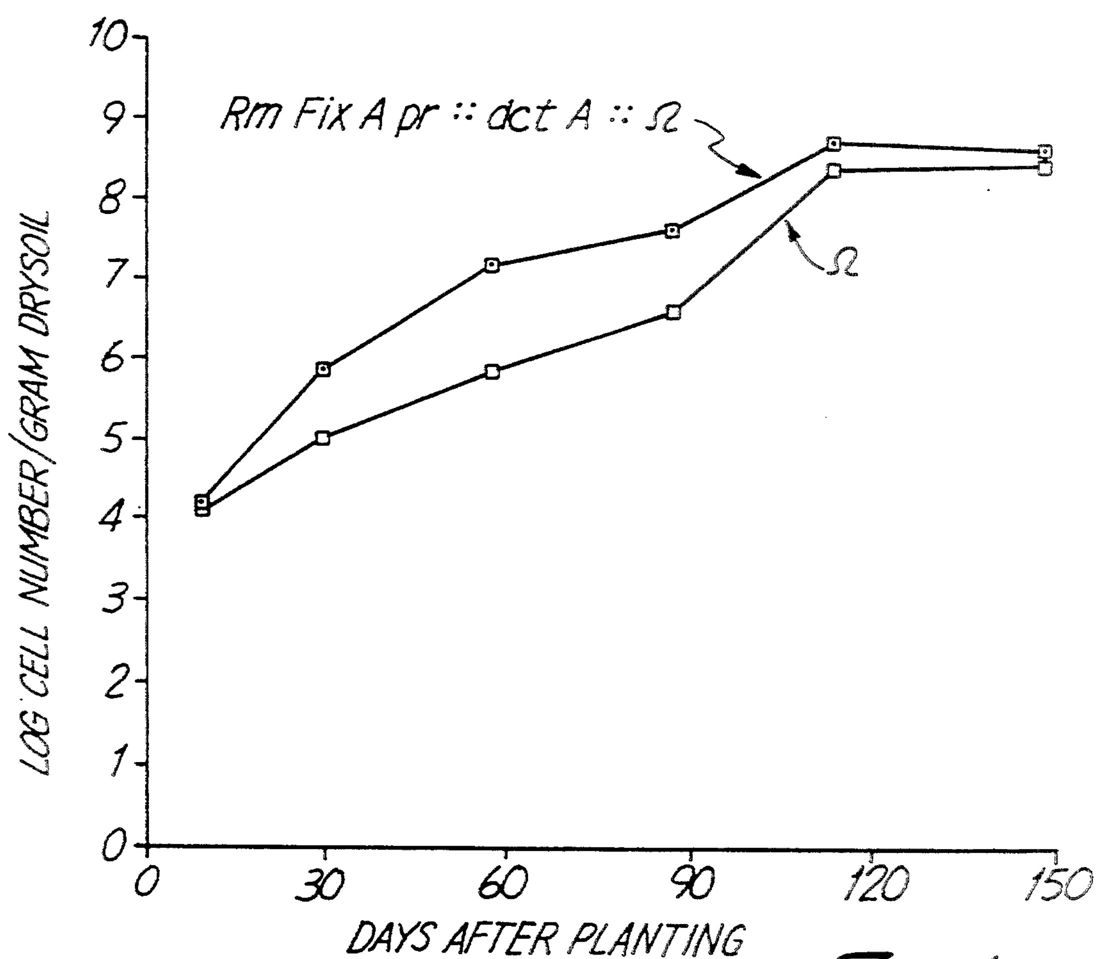
FIG. 16 is a graph of the effect of time after planting on cell number of *B. japonicum* in the inner rhizosphere.
Figure 17:
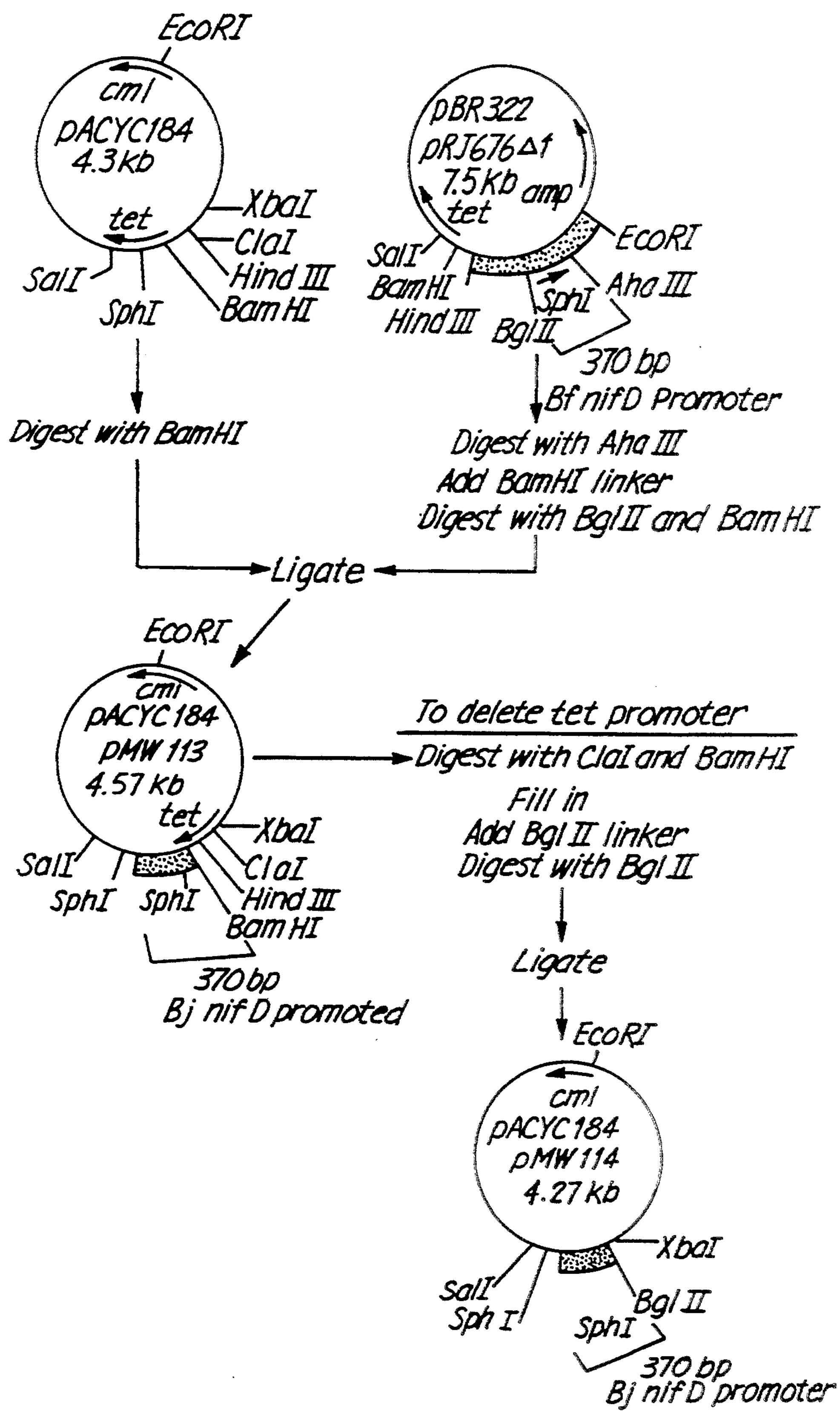
FIG. 17 is a summary of the construction of pMW114.

FIG. 16 plots the number of cells per gram of dry soil from the inner rhizosphere as a function of day after planting. BJB1003 carries a RmfixApr::dctA::Ω cassette (solid rectangles) and BJB1001 carries a Ω cassette (closed rectangles). The *B. japonicum* populations in the soybean rhizosphere grew more rapidly than the plant root throughout the course of plant development. Populations increased from $1\times10^4$ to $1\times10^9$ cells per gram dry inner rhizosphere soil between Days 9 and 115 following planting. The increase slowed considerably after Day 115, as plants senescence during the R7 stage. Similar trends were also observed in the outer rhizosphere, although the growth curves were considerably less linear, and the late-season shift in population growth was not evident. As shown in FIG. 16, statistically significant increases were observed in rhizosphere establishment of BJB1003 over BJB1001. The data in FIG. 16 suggest that the difference between the BJB1001 and BJB1003 population profiles in the inner rhizosphere may be attributed to more rapid establishment by BJB1003 during the first 58 days of plant development.

EXAMPLE 3

Improved Rhizosphere Colonization of Pseudomonas Strains Isolated From the soybean Rhizosphere Methods and/or materials described herein can be used to increase the competitiveness of other rhizospheric bacteria, e.g., Pseudomonas species. To determine whether increased expression of dctA improves the rhizosphere colonizing ability of a rhizosphere-competent Pseudomonas strain, a dctA expression cassette can be integrated into the chromosome of the Pseudomonas strain, and the ability of the resultant strain to colonize soybean roots determined and compared to that of its parent strain.

Cassettes described above, preferably either the nptIIpdctA::Ω cassette, or the dctABD::Ω cassette, can be used as the starting material. Alternatively the dctABD genes may be isolated from the Pseudomonas strain of interest by methods known to those skilled in the art, e.g., by the methods described above, and used in place of the dctA or dctABD genes from *Rhizobium leguminosarum.*

Transformation of the gene cassette into the Pseudomonas strain of choice, and integration of the cassette into the host chromosome, can be accomplished by methods known to those skilled in the art, e.g., by using a plasmid vector of the type described in Barry (1986), supra. Specifically, synthetic HindIII linkers can be ligated into the HpaI site of pMON7020, (Barry (1986) supra), resulting in a plasmid with a unique HindIII site between the Tn7 ends (which are required for the integration of the foreign genes) contained on pMON7020. The resulting plasmid, referred to herein as p7020H, will be analogous to pMON7022 described by Barry, except that it will contain a HindIII site in place of the BamH1 site of pMON7022. A dct cassette is then cloned as a HindIII fragment and inserted into p7020H to give p7020HdctABD::Ω or p7020HnptIIPdctA::Ω. These plasmids can then be used to transform the dct cassette into the Pseudomonas strains of choice, using methods known to those skilled in the art, e.g., methods analogous to those used in Barry (1086) supra, to integrate the lacZY genes carried on pMON7029 into the chromosome of *P. fluorescens* strain 701E1Rif$^R$, a spontaneous rifampicin resistant derivative of a wild type isolate.

Selection is made for the streptomycin and spectinomycin resistances carried on the Ω fragment (which is part of the dct cassette), rather than for lactose utilization as was used in Barry (1986), supra. Specifically, pMON7018 helper (Km$^R$) and p7020HdctABD::Ω or p7020H nptIIpdctA (Str$^R$SpC$^R$TC$^R$) are introduced into *P. flouresens* 701E1Rif$^R$ by triparental matings using pRK2013 as the helper plasmid (Figurski (1979), supra; Ditta et al. (1988), supra). Pseudomonas exconjugants containing both plasmids are selected on media containing rifampicin, kanamycin, streptomycin, and spectinomycin. Purified exconjugants are grown for 50 generations on minimal succinate +Km+Str+Spc medium, to allow the transposition event to occur, followed by 15 generations in minimal succinate +Str+Spc medium, to allow loss of pMON7018. Single colonies are then screened to identify those that are Str$^R$Spc$^R$Km$^s$Tc$^s$. These colonies should have lost the pMON7018 and p7020HdctABD::Ω or p7020HnptIIpdctA replicons and contain the dct cassette integrated into the chromosome. DNA is then made from a few such colonies, digested with EcoR1, run on an 0.8% agarose gel, blotted to a nylon or nitrocellulose membrane, and probed with radiolabelled dctABD DNA to identify strains in which the dct cassette has integrated into the chromosome.

To determine whether the *R. leguminosarum* dctABD genes may be used, or whether it is preferable to use another construction for the expression of dctA, e.g., the nptIIpdctA fusion gene, or a construction containing the dctABD genes from the Pseudomonas strains of interest, it is necessary to know whether the *R. leguminosarum* dctABD genes are expressed in the Pseudomonas strains of interest. This can be determined by introducing plasmid pCR63 (Ronson et al., (1987) *J. Bact.* 169:2424–2431, hereby incorporated by reference) which contains the dctA gene from *R. leguminosarum* fused to lacZ, and wild-type copies of the *R. leguminosarum* dctB and dctD genes, into the Pseudomonas strains of choice. The resultant strain is then plated on minimal medium plus succinate plus X-gal. If the *R. leguminosarum* genes are expressed the strain should form deep blue colonies on the medium containing succinate and X-gal. If the colonies formed on succinate plus X-gal are light blue or white it is likely that the *R. leguminosarum* dctABD genes are not efficiently expressed in the Pseudomonas strains. In this case it is preferable to isolate the dctABD genes from the Pseudomonas strains of choice. As is known to those skilled in the art, the method of fusing the lacZ gene to the gene of interest can be used as a general method for determining whether a given construction is suitably expressed in a given host.

The Pseudomonas strains of choice in this example can be any Pseudomonas strains capable of growth in the soybean rhizosphere and capable of exerting a beneficial effect on plant growth, preferably soybean growth, e.g., *Pseudomonas aureofaciens,* ATCC43051, (ATCC, Bethesda, Md.). A bacterium of the genus Xanthomonas can also be used.

Methods for comparing the root colonization ability of two strains are well known to those skilled in the art. In one method, approximately equal numbers of the two strains, the parent strain and the dct derivative, each marked with rifampicin-resistance (Rif$^R$), are added to soybean seeds at a rate of $10^5$ bacteria per seed. The seeds are then planted in pots containing soil or an artificial substrate of choice in a greenhouse. After three weeks of growth the plants are harvested and their root systems are processed as described in Example 2. The rhizosphere wash is then serially diluted onto medium containing rifampicin, and rifampicin-resistant colonies of the appropriate morphology are then patched onto medium containing streptomycin and spectinomycin. If the ratio of the Str$^R$SpC$^R$Rif$^R$ bacteria to Rif$^R$ bacteria is greater than 0.5, then the dct derivative has improved competitive ability over its parent strain. A control experiment with seeds that have not received a bacterial inoculation is run to correct for the number of Rif$^R$ bacteria that are not the inoculant strain. For the experiment to provide useful data, this number should be at least 10-fold less than obtained in the experiment done with inoculated seed.

EXAMPLE 4:

Increased Competitiveness of Rhizobia for Nodule Occupancy (Greenhouse studies)

The presence of certain microbes in the rhizosphere, may benefit a plant, e.g., by producing a pesticide or fixing nitrogen for the plant. If such a microbe also exhibits an increased competitive advantage for growth within the rhizosphere, the benefit may be maximized. Nitrogen fixing strains which over-express dctA have a competitive growth advantage which results in increased representation in the rhizosphere and in increased nodule occupancy. Elevated nodule occupancy by these strains should result in maximal nitrogen fixation effects. In the experiments described below dctA over-expressing strains were co-inoculated with other laboratory and native strains of Rhizobia or Bradyrhizobia, and the relative contribution of each to nodule population determined.

The Rhizobia or Bradyrhizobia strains were grown in LB (LB=10g/l Bacto-tryptone, 5 g/l bacto-yeast extract, and 10 g/l NaCl, ph 7.5) (*R. meliloti*) or RDM (*B. japonicum*) to a density of $10^8$–$10^9$ cells/mi. Cells were harvested, pelleted, washed 1 time in $H_2O$ and resuspended in sterile distilled water. Cell numbers were confirmed at the beginning of the experiment by optical density measurements and the percentage of viable cells subsequently determined by plate assays. The viable counts determined by the plate assays were used to determine cell ratios.

The competition assays were conducted in sterile vermiculite and native soils from specific midwestern field locations which contain different levels of indigenous strains of nitrogen fixing bacteria and therefore different degrees of competitive pressure. Seeds were planted in vermiculite alone or in a 2:1:1 mixture of soil/vermiculite/perlite. Inoculants were applied directly to the seeds, in water, at a concentration of approximately $10^5$ cells/seed. In the case of dual inoculants, both strains were present in the inoculum at the time of seed treatment.

Occupancy of root nodules was assessed from a minimum of 96 nodules per treatment as follows: Nodules were removed from 3–5 week old plants and surface sterilized by immersion for 1 minute in 50% bleach followed by 3 water rinses. The nodules were then crushed and plated onto both selective and non-selective media. The genetically-engineered strains were identified as $Spc^r/Sm^r$ due to the presence of the Ω fragment. In the case of *Bradyrhizobium japonicum*, the strains were plated on non-selective medium of RDM containing the fungistats cyclohexamide (75 μg/ml) and nystatin (75 μg/ml). The selective medium contained spectinomycin (1000 μg/ml) and streptomycin (200 μg/ml) as well as the fungistats. When the assays using *B. japonicum* were conducted in soil a third medium was used which contained the fungistats plus rifampicin (50 μg/ml) in order to distinguish the non-engineered inoculant strains, which are intrinsically rifampicin resistant, from the indegenous rif sensitive strains. The non-selective *R. meliloti* medium was LB plus the fungistats and the selective medium was supplemented with spectinomycin (100 μg/ml) and streptomycin (100 μg/ml). For *R. meliloti*, laboratory strains could easily be distinguished from native Rhizobia by colony morphology since the native Rhizobia indigenous to the soils used have a mucoid morphology, whereas the laboratory strains do not.

Soybean nodule occupancy

*B. japonicum* is the nitrogen fixing bacteria associated with soybeans. In most natural settings where soybeans are grown there are significant numbers of wild type *B. japonicum* in the soil. Seeds were planted in soil and inoculated either pairwise or individually. In the single inoculants the ability of the inoculant strain to out-compete the indigenous strains was determined. In the case of the dual inoculants, the engineered strains were tested against their non-engineered parents as well as the indigenous strains. The strains were also tested pairwise in sterile vermiculite.

The data summarized in Table 1A compare the competitiveness of a strain carrying a Rm fixA pr::dctA::Ω fusion integrated at the RSα9 site of BjPC (BJB2003) with the non-engineered parent (PC). A control strain was also constructed which carries only the Ω marker integrated at the same site (BJB2001), and its competitiveness assayed relative to the parent. This experiment was conducted in sterile vermiculite. The engineered strain carrying only the Ω insert (BJB2001) shows similar nodule occupancy to the parent (PC) establishing that the presence of the Ω fragment alone has no significant effect on competitiveness. In contrast, the strain containing the Rm fixA pr::dctA;;Ω cassette (BJB2003) out-competed the parent with the dct enhanced strain occupying 92% of the nodules vs. 8% for the non-engineered parent.

TABLE 1

The Effect of dct Over-expression on Competitiveness in *B. japonicum*

| Strains | Insert | cells/seed | % nodule occupancy |
|---|---|---|---|
| A. Liquid co-inoculation in vermiculite | | | |
| BJB2001 | Ω | $1.0 \times 10^5$ | 42 |
| PC | | $1.0 \times 10^5$ | 58 |
| BJB2003 | fixA::dctA | $1.0 \times 10^5$ | 92 |
| PC | | $1.0 \times 10^5$ | 8 |
| B. Liquid co-inoculation in Sun Prairie soil | | | |
| BJB1001 | Ω | $1.1 \times 10^3$ | 4 |
| 110 | | $1.6 \times 10^3$ | 17 |
| indigenous | | | 79 |
| BJB1003 | fixA::dctA::Ω | $2.5 \times 10^3$ | 36 |
| 110 | | $1.3 \times 10^3$ | 0 |
| indigenous | | | 64 |
| BJB1001 | Ω | $1.1 \times 10^5$ | 7 |
| 110 | | $1.6 \times 10^5$ | 19 |
| indigenous | | | 74 |
| BJB1003 | fixA::dctA:Ω | $2.5 \times 10^5$ | 50 |
| 110 | | $1.3 \times 10^5$ | 25 |
| indigenous | | | 25 |
| C. Single Inoculants in Sun Prairie Soil | | | |
| BJB1001 | Ω | $2.0 \times 10^5$ | 33 |
| indigenous | | | 67 |
| BJB138ΩKB | dctABD/Ω | $5.0 \times 10^3$ | 66 |
| indigenous | | | 34 |
| BJB2001 | Ω | $9.8 \times 10^5$ | 19 |
| indigenous | | | 81 |
| BJB2003 | fixA::dctA/Ω | $1.1{\times}10^6$ | 57 |
| indigenous | | | 43 |

Similar experiments were also performed in soil isolated from Sun Prairie, Wisconsin to determine whether the strains are competitive in a soil environment which contains indigenous Bradyrhizobium strains as well as other rhizosphere organisms which may affect nodule occupancy of the inoculant strains. The data from this experiment is summarized in Table 1B. In this case the engineered strains were derivatives of strain I-110. They otherwise are identical to the comparable PC derivatives tested in vermiculite in the previous experiment. The inoculants were applied pairwise comparing the non-engineered parent (110) with either the dct enhanced strain (BJB1003, which carries a fixA pr::dctA::Ω cassette) or a strain carrying only the Ω marker (BJB1001). The strains were applied at a rate of either $10^3$ or $10^5$ per seed in order to test the effect of inoculant rate on the ability to out-compete the indigenous strains. At $10^3$ cells per seed BJB1001 (Ω) and 110 together occupied only 21% of the nodules. The dct engineered strain (BJB1003) out-competed its parent (36% vs. 0%) but was still unable to totally out-compete the indigenous strains which occupied 64% of the nodules. Increasing the inoculant rate to approximately $10^5$ cells of each strain had little effect on the ability of the BJB1001 (Ω)+110 pair to out-compete the indigenous strains with the indigenous strains occupying 74% of the nodules while BJB1001 and 110 occupied 7 and 19% of the nodules respectively. The dct engineered strain (BJB1003) out-competed both the indigenous strains plus the parent strain (110) when applied at the higher rate. The competitiveness of the dct engineered strains when applied as single inoculants was also assessed in Sun Prairie soil (Table 4C). Strain BJB2003 (fixA pr::dctA::Ω insert) was about three-fold more competitive than BJB2001 (Ω) versus the indigenous strains. In addition to the strains in which the introduced dctA gene was expressed from the Rm fixA promoter (BJB1003 and BJB2003) another Bj 110 dct derivative was tested. Strain BJB138ΩKB carries all three dct genes from *R. leguminosarum*, dctABD, expressed from their native promoters. In this case the Ω engineered strain, BJB1001, occupied 33% of the nodules. The dctABD engineered strain (BJB138ΩKB) was twice as competitive as BJB1001 (66% vs. 33%) even though it was applied at 1/100th the rate ($2\times10^5$ vs. $5\times10^3$ cells/-seed).

In summary, over-expression of the dctA gene increased the competitive ability of the recombinant strain with respect to the non-engineered parent. The difference was most apparent when the strains were tested as co-inoculants, both in vermiculite and in soil containing an indigenous *B. japonicum* population. The increased competitiveness was also observed when the strains were inoculated singly, although the differences were not as great as that observed in the co-inoculants.

Alfalfa nodule occupancy

Competition experiments similar to those described for soybean were also done with alfalfa. *R. meliloti* is the nitrogen fixing bacteria associated with alfalfa. Each of the dct engineered *R. meliloti* strains was co-inoculated with the non-engineered parental strain, RCR2011, using a liquid application at the time of planting. The results are shown in Table 2.

TABLE 2

The Effect of an Extra Copy of the dct Genes on Competitiveness of *R. meliloti*

| Strains | dct/2011 Ratio | % Nodule Occupancy Vermic. | Sun Prairie | River Falls | Rio |
|---|---|---|---|---|---|
| RMB138Ω710A* | 1/1.1 (verm.) | 63 | 75 | 40 | |
| RCR2011 | 1/1.9 (soil) | 32 | 24 | 15 | |
| indigenous | | | 1 | 45 | |
| RMB125Ω710A** | 1/8.6 | 94 | 88 | 31 | 90 |
| RCR2011 | | 6 | 12 | 5 | 5 |
| indigenous | | | 0 | 64 | 5 |

* = strain carries dctABD (P3, A)
** = strain carries nptII::dctA (P3, A)

The alfalfa seeds were planted in sterile vermiculite or different soils with different levels of indigenous strains. The Sun Prairie and Rio soils contain relatively low levels of indigenous *R. meliloti* and have approximately 10 and 250 cells per gram of soil respectively. The River Falls soil is much more competitive and contains approximately 4100 *R. meliloti* cells/gram of soil.

Two dct enhanced derivatives of RCR2011 were tested. RMB138Ω710A contains the dctABD genes expressed from their own promoters. Strain RMB125Ω710A contains the dctA gene expressed constitutively from the nptII promoter. Both derivatives also contain the Ω marker as part of the enhancement cassette which was integrated into the P3 site. The strains are described in more detail in Example 1. The dctABD engineered strain (RMB138Ω710A) out-competed its parent (RCR2011) in vermiculite and both soils tested. It also out-competed the indigenous strains in Sun Prairie soil, but not in River Falls where the engineered strains showed equal nodule occupancy with the indigenous strains. The engineered strain which expressed dctA constitutively from the nptII promoter (RMB125Ω710A) was even more competitive than the strain which over-expressed the dct genes from the native promoters. Strain RMB125Ω710A out-competed the parent (RCR2011) by up to 20-fold in soil and vermiculite. This was true even though the parent strain was present in the inoculum at a 9-fold higher rate than the engineered derivative.

EXAMPLE 5:

Increased Nodule Occupancy Competitiveness of *Bradyrhizobium japonicum* (field trials)

*B. japonicum* strains containing an engineered dctA gene were tested for their ability to competitively nodulate soybeans in the field. Centennial and Braxton, two commercially available soybean cultivars were employed as host plants. Both of these cultivars are grown extensively for soybean production in the southeastern U.S.

Cell preparation, inoculation and planting were as described for rhizosphere competition described above. Nodule occupancy was determined as described under soybean greenhouse studies above.

Strains BJB1003 and BJB2003 were tested for nodule occupancy relative to the control strains BJB1001 and BJB2001 respectively. Strains BJB1003 and BJB2003 were engineered to express the recombinant dctA gene from the RmfixA promoter and carry the RmfixA pr::dctA;;Ω cassette integrated into the RSα9 site of Bj110 and BjPC respectively. The control strains, BJB1001 and BJB2001, carry only the Ω marker integrated at the RSα9 site of Bj110 and BjPC respectively. The strains are more thoroughly described in Example 1.

The dct engineered strains BJB1003 and BJB2003 were compared with the Ω engineered control strains BJB1001 and BJB2001, respectively, on two soybean cultivars, therefore four separate comparisons were possible. The results are shown in Table 3.

TABLE 3

Inoculant Nodule Occupancy
1989 *B. japonicum* Strains Comparison Trial

| Strain | Soybean Variety | Average % Occupancy |
|---|---|---|
| BJB1001 | Braxton | 38 |
| BJB1001 | Centennial | 17 |
| BJB1003 | Braxton | 38 |
| BJB1003 | Centennial | 27 |
| BJB2001 | Braxton | 32 |
| BJB2001 | Centennial | 32 |
| BJB2003 | Braxton | 66 |
| BJB2003 | Centennial | 64 |

In each case the inoculant was applied singly and was competing against the indigenous strains in the field. In three out of the four cases the dct enhanced strain was more competitive against the indigenous strains than the control (BJB2003 vs. BJB2001 on Braxton and Centennial and BJB1003 vs. BJB1001 on Centennial). In one case no difference was observed (BJB1003 vs. BJB1001 on Braxton).

EXAMPLE 6:

Effect of dct Over-expression on Nitrogen Fixation in Alfalfa

The effect of dct engineering on symbiotic nitrogen fixation of *R. meliloti* was determined in the greenhouse in plants grown in sterile nitrogen-free vermiculite, by methods known to those skilled in the art. Rhizobium were grown in shake flasks to a density of $10^9$ cells/ml or greater, pelleted, washed twice with distilled water and then re-suspended in distilled water. Alfalfa seeds were sown in 4.5 inch pots filled with sterile vermiculite using approximately 1 gram of seeds per pot and inoculated with a minimum of $10^5$ cells/seed at planting by pouring the cells directly onto the seeds. A minimum of 10 pots for each treatment was used in each experiment. The plants were watered as necessary and supplemented weekly with a nitrogen-free nutrient solution. The above-ground biomass was harvested at three weeks and dry weights determined. Since the plants were grown under nitrogen-free conditions the biomass produced is directly proportional to the nitrogen fixing ability of the inoculant strain. For the data summarized in Table 4 the biomass of plants inoculated with dct enhanced strains was compared with that produced by plants inoculated with the non-engineered parent strain, RCR2011.

Expressing dctA constitutively from the nptII promoter produced yield increases of 5 to 6% when integrated at the P3 locus (RMB125Ω710A). The strain over-expressing the dctA gene from its own promoter at the P3 locus (RMB139Ω710A) was the most symbiotically effective with statistically significant yield increases of 13% and 7% over RCR2011 achieved in two separate experiments. Expressing the regulatory genes in addition to the transport gene had no additional effect on nitrogen-fixation over that observed in the dctA integrant, RMB139Ω710A. A strain carrying the dctABD cassette at the P3 locus (RMB138Ω710A) showed a statistically significant yield increase of 10% relative to RCR2011 in one experiment and 3% in a second experiment. Therefore, in addition to enhancing competitiveness, over-expressing the dctA gene also increases symbiotic nitrogen fixation in the engineered strains.

TABLE 4

The Effect of dct Over-expression on Symbiotic Nitrogen Fixation in *R. meliloti* RCR2011

| Biomass Strain | dct Integrant | Site/Orientation | Alfalfa vs. RCR2011 |
|---|---|---|---|
| RMB125Ω710A | nptII pr::dctA | P3, oriA | +5%, +6% |
| RMB138Ω710A | dctABD | P3, oriA | +10%**, +3% |
| RMB139Ω710A | dctA | P3, oriA | 13%**, +7%* |

**Statistically significant ($P < 0.01$) difference
*Statistically significant ($P < 0.05$) difference

EXAMPLE 7 dct plus nifA Enhanced Strains

In some cases it is desirable to engineer multiple traits into a given strain, e.g., to integrate engineered derivatives of a first gene or set of genes which enhance one desirable trait, and a second gene or set of genes which enhances another desirable trait into a strain. To produce strains enhanced for both dct-engendered competitiveness and for nitrogen-fixation, both dct expressing cassettes and nifA expressing cassettes were integrated into strains. The cloning of nifA is described in Beynon et al., European Patent Application 0 339 830, hereby incorporated by reference.

The genes can either be integrated as a single cassette or integrated individually as two separate cassettes, in two different sites. The two sites used in this example are the *R. meliloti* P3 (described in example 1) and inositol (described below) sites. The nifA and dctA genes may be expressed in a variety of ways using different promoter::gene fusions. The recombinant strains described in this example involve the *R. meliloti* nifA gene expressed from the *B. japonicum* nifD promoter and the dctABD genes from *R. leguminosarum* expressed from the wild-type dct promoters. The dctABD locus from *R. leguminosarum* was described in example 1. The strains described in this example contain 1) a single nifA/dctA dual cassette integrated at the P3 or the inositol locus, or 2) a nifA cassette integrated at the P3 locus and a dct cassette integrated at the inositol locus. Alternatively the integration site of the two cassettes can be reversed.

Enhancement Cassettes

Three enhancement cassettes were constructed. Each includes the nifA and/or dctA gene plus an antibiotic resistance marker. The dual nifA/dctA cassette contains the Ω marker which encodes spectinomycin and streptomycin resistance (see example 1). In order to easily integrate two enhancement cassettes, different antibiotic resistance markers were used in each cassette in the case of applications that require integration of two cassettes into the host chromosome. The dctA cassette includes the Ω marker while the nifA cassette includes a derivative of the nptII gene which specifies kanamycin and neomycin resistance.

dctABD/Ω Cassette The dctABD/Ω HindIII cassette is contained on plasmid pRK138Ω and is described in example 1.

nifA/nptII Cassette The *B. japonicum* nifD promoter was fused to the *R. meliloti* nifA gene using the untranslated leader region of *R. meliloti* nifH between the transcriptional and translational start sites. The final fusion therefore contains the *B. japonicum* nifD promoter upstream of the +1 of transcription, the *R. meliloti* nifH leader from the +1 of transcription to the +1 of translation followed by the *R. meliloti* nifA coding region. The nifA fusion in the cassette is bracketed by the nptII gene (which specifies neomycin resistance), and by the T1T2 terminator. The construction of the complete cassette is outlined in FIG. 12–20.

Subcloning of the *B. japonicum* nifD promoter The source of the *B. japonicum* nifD promoter was pRJ6761$_{\Delta 1}$, a derivative of pRJ676 (Hennecke, (1981) *Nature* 291:354–355, hereby incorporated by reference; Fuhrman and Hennecke, (1982) Mol. Gen. Genet. 187:419–423, hereby incorporated by reference) created by digestion of pRJ676 with EcoRI followed by self-ligation. Analysis of the sequence of the *B. japonicum* nifD gene (Kaluza and Hennecke (1984) Mol. Gen. Genet. 196:35–42, hereby incorporated by reference) revealed an AhaIII site 9 bp upstream of the translational start site and a BglII site 365 bp further upstream. These sites were used for subcloning the nifD promoter (See FIG. 17). pRJ676$_{\Delta 1}$ was digested with AhaIII, BamH1 linkers added, the mixture digested with BamHI and BglII, and the 365 bp fragment isolated and cloned into pACYC184 (Chang et al., (1978) *J. Bact.* 134:1141–1156, hereby incorporated by reference) cut with BamHI, giving pMW113. pMW113 was then deleted of the plasmic tet promoter by digestion with ClaI and BamHI, BglII linkers added and re-ligated to yield pMW114. The *B. japonicum* nifD promoter and leader sequence can be isolated, together with ~200 bp of tet gene sequence (in reverse orientation to the promoter) from pMW114 as a SphI-BglII fragment.

Figure 18:
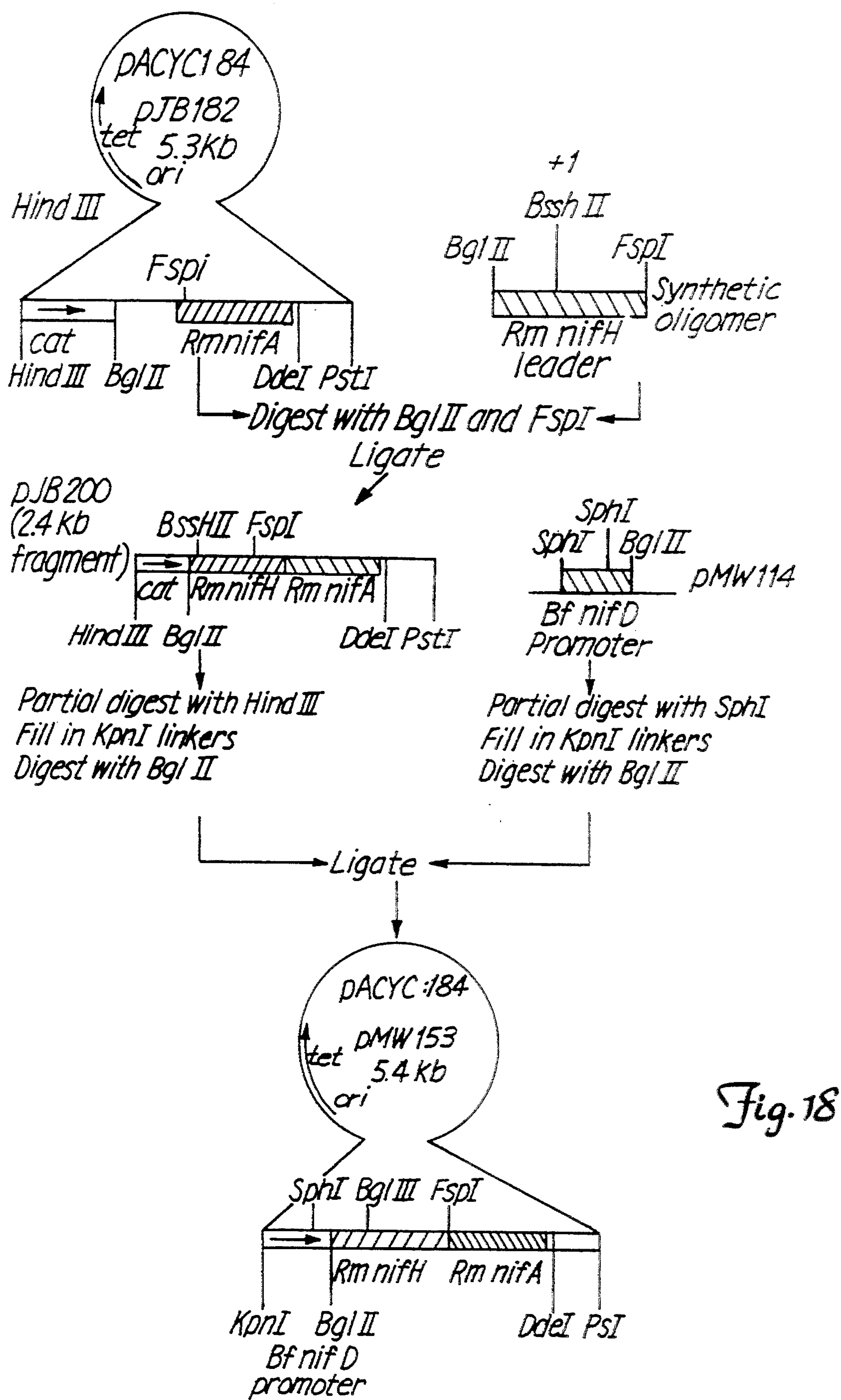
FIG. 18 is a summary of the fusion of the *R. meliloti* nifH leader sequence to the *R. meliloti* nifA coding sequence, and addition of the Bj nifD promoter.

Fusion of the *R. meliloti* nifH leader sequence to the *R. meliloti* nifA coding sequence and addition of the *B. japonicum* nifD promoter The construction of this fusion is summarized in FIG. 18. The source of the *R. meliloti* nifA gene for this construction was pJB182 (Beynon et al. (1988) *EMBO J.* 7:7–14, hereby incorporated by reference). pJB182 includes the *R. meliloti* nifA gene fused to the cat promoter, cloned as a HindIII-PstI fragment into pACYC184. As part of the construction of pJB182, the XmnI site of pACYC184 was converted, using linkers, to a HindIII site. The *R. meliloti* nifA gene contains a FspI site at the fist codon of its coding sequence, while the cat promoter in pJB182 contains a BglII site upstream of the transcriptional start site. An oligonucleotide linker (see Table 5 for its sequence and derivation) was synthesized with the sequence of the *R. meliloti* nifH leader region with FspI and BglII ends and inserted into pjB182, giving pJB200.

TABLE 5

| Derivation of the nucleotide sequence of Bj nifD::Rm nifA fusion gene | |
|---|---|
| pBR322 tet gene non-coding strand | KpnI<br>1 GGTACCCATGC (Nucleotides 560→381 from Appendix B in Molecular Cloning: A laboratory Manual, Maniatis et al., Cold Spring Harbor Laboratory, 1982, hereby incorporated by reference) 193 (Sequence I.D. No. 4) |
| BamHI/Bg1II splice | GGATCT |
| Bj nifD promoter | [Nucleotides −379→−70 from FIG. 2 in Kaluza et al., (1984) Mol. Gen. Genet. 196:35-42, hereby incorporated by reference] (Sequence I.D. No. 5) |
| Bj nifD promoter | GCATGCCGGTTGCAAAGTCTTGG (Sequence I.D. No. 6) |
| [Bj nifD/Rm nifH linker sequence] | ccggttgcaaagtcttggggg (Sequence I.D. No. 7) |
| Rm nifH leader | GGG<br>[Nucleotides +4→69 from FIG. 3 in Sundaresen et al., (1983) Nature 301:728-73, hereby incorporated by reference] (Sequence I.D. No. 8) |
| [Rm nifH/Rm nifA linker sequence] | gatctcg(nts +4→69 from FIG. 3 in Sundaresen et al., (1983) Nature 301:728-73, hereby incorporated by reference (Sequence I.D. No. 8) |
| Rm nifA coding sequence | ATG [Nucleotides +4→1622 from FIG. 2 from Buikema et al. (1985) Nucl. Acids Res. 13:4539-4555, hereby incorporated by reference] (Sequence I.D. No. 9) |
| Post C-terminal polylinker sequence | Termination codon<br>CTAAGACTAGTCGGTGAGATAAA--(Sequence I.D. No. 10)<br>DdeI<br>GGCGTCGCAGATCGCTGGTACC_(Sequence I.D. No. 11)<br>KpnI |

The sequences of the linkers used in the construction are shown in lower case.

The *B. japonicum* nifD SphI-BglII promoter fragment was then added to pJB200 and at the same time a KpnI site was constructed at the 5′ end of the promoter. pMW114 was partially digested with SphI, KpnI linkers were added, the mixture was digested with KpnI and BglII, and the appropriate-sized fragment was isolated. pJB200 was partially digested with HindIII, KpnI linkers were added and the mixture was digested with KpnI and BglII and the appropriate-sized fragment was isolated. The fragments from pMW114 and pJB200 were ligated together, giving pMW153. pMW153 contains the *B. japonicum* nifD promoter and leader sequence and the *R. meliloti* nifH leader sequence.

Figure 19:
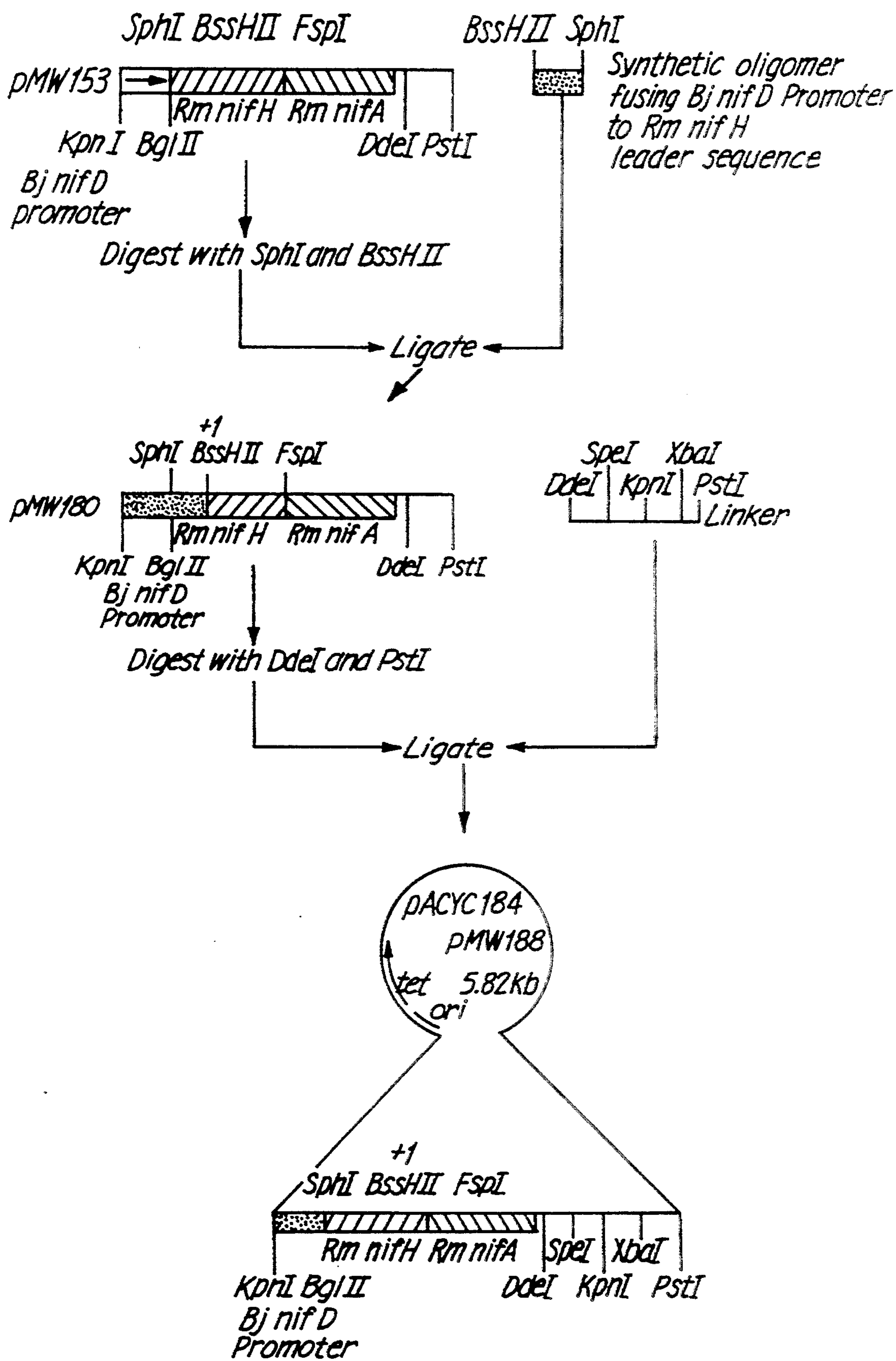
FIG. 19 is a diagram of the construction of pMW188.

Construction of the fusion gene To construct an exact fusion at the +1 of transcription of the *B. japonicum* nifD promoter and *R. meliloti* nifH leader, a 21 bp oligomer (See Table 5) with SphI-BssHII ends was added to SphI-BssHII digested pMW153, giving pMW180, as shown in FIG. 19. pMW180 contains the *B. japonicum* nifD promoter fused precisely at the +1 of transcription to the *R. meliloti* nifH leader sequence which is in turn fused at the +1 of translation to the *R. meliloti* nifA gene. To enable the fusion gene to be isolated as a KpnI fragment, a linker encoding a KpnI site (as well as SpeI and XbaI sites) was added between the DdeI and PstI sites at the 3' end of the nifA gene, giving pMW188, as shown in FIG. 19.

Figure 20:
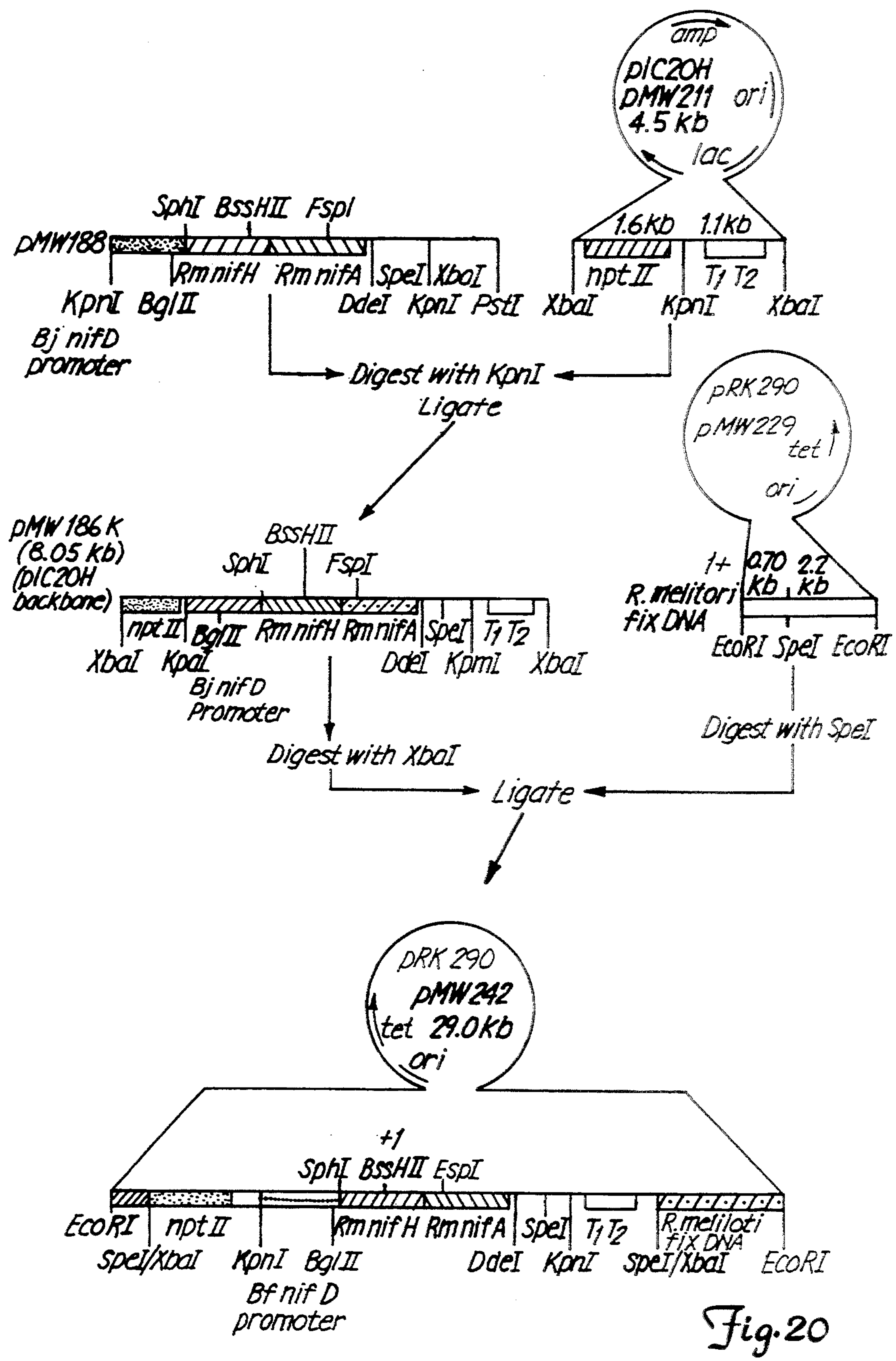
FIG. 20 is a diagram of the construction of pMW242.

Addition of TIT2 Terminators and the nptII Gene The T1T2 terminators and the nptII gene were added to the nifA fusion via plasmid pMW211, see FIG. 20. pMW211 was constructed as follows. The T1T2 terminators were isolated as an 1100 base pair PvuII fragment from pEA300 (Brosius et al. (1981) J. Mol. Bio. 148:107–127, hereby incorporated by reference) and cloned into the SmaI site of pIC20H forming plasmid pMW157. The nptII gene was isolated on a 1.6 kb EcoRI fragment from plasmid pUC4-K1XX, obtained commercially (Pharmacia), and cloned into EcoRI-digested pMW157 to give pMW211.

The *B. japonicum* nifD::nifH::nifD fusion gene was cloned into the KpnI site of pMW211, giving pMW186K. The fusion gene, flanked by T1T2 terminators and the nptII gene is therefore present as an XbaI cassette in the pIC20H backbone of this plasmid.

Figure 21:
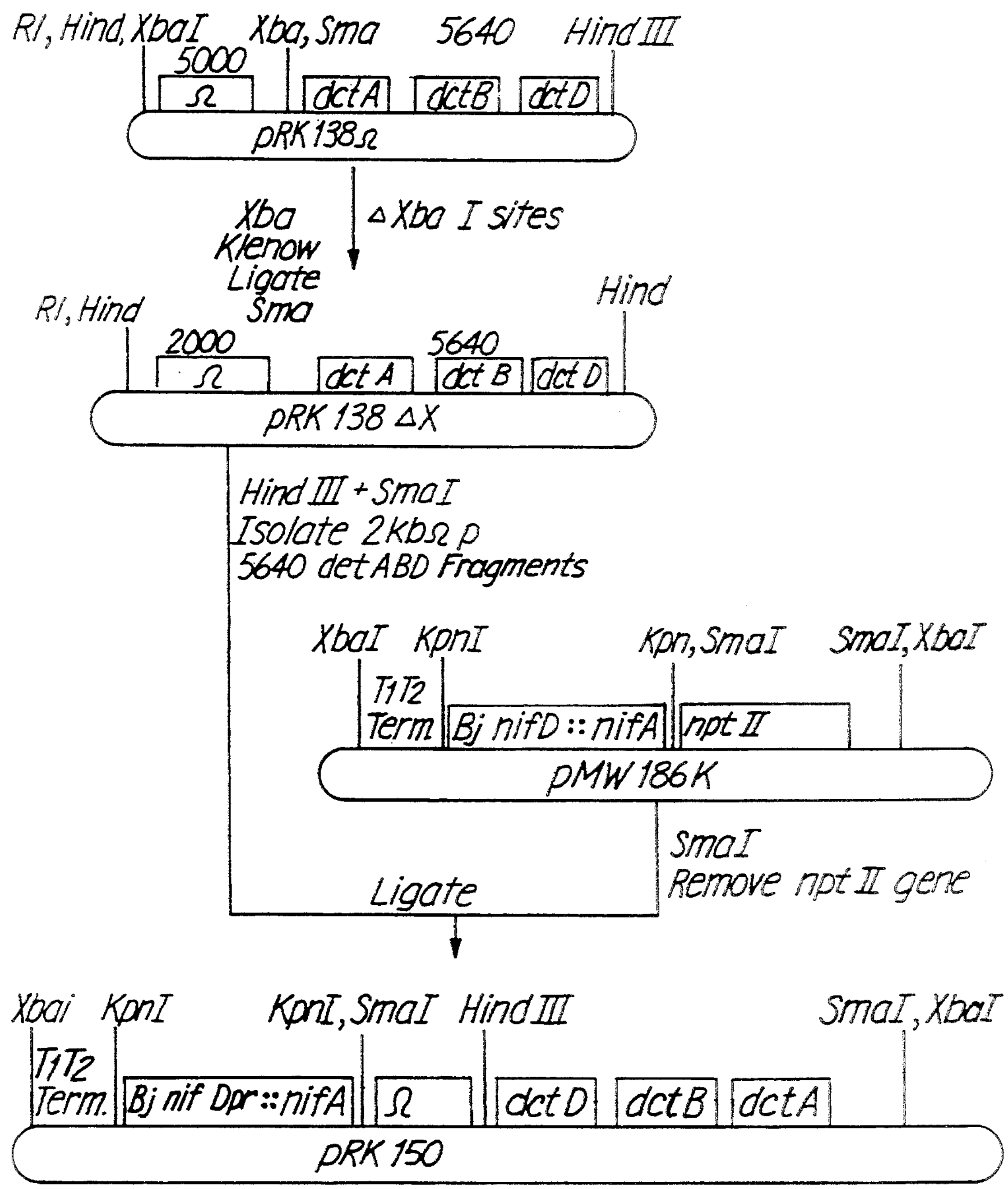
FIG. 21 is a diagram of the construction of pRK150.

The nifA/Ω/dctA Dual Cassette The construction of the dual cassette is outlined in FIG. 21. The nifA fusion was carried on a pIC20H backbone in plasmid pMW186K, described above. The dctABD genes, plus the Ω fragment, were obtained from pRK138Ω, described above. The cassette was designed to be ultimately excised using XbaI sites. Therefore the XbaI sites in pRK138Ω were removed by digesting with XbaI, filling in the ends with Klenow enzyme, and re-ligating to form pRK138ΩΔX. Plasmid pRK138ΩΔX was digested with HindIII plus SmaI, the 2000 base pair Ω fragment and the 5640 base pair dctABD containing fragment isolated, and both fragments inserted into SmaI cut pMW186K. The final XbaI cassette is contained on pRK150 (FIG. 21). Note that in order to place the dctA terminator at one end of the cassette the orientation of the Ω fragment with respect to the dct genes has been reversed with respect to that in pRK138Ω. The dctA terminator and T1T2 terminator therefore bracket the remainder of the cassette.

Integration Sites and Integration Vectors

The P3 Integration Site The P3 integration site, and vector pCR710, were described in example 1. pCR710 was further modified by converting the unique HindIII site to an SpeI site by adding linkers to form pMW229. This allowed the insertion of SpeI or XbaI cassettes into the integration site. (Note that SpeI and XbaI digestion produces ends that can be ligated although the junction cannot be recut by either enzyme.)

The Inositol Integration Site To identify a symbiotically silent region of the *R. meliloti* genome for the integration of the constructs, a catabolic pathway that, a priori, was not expected to affect either the free-living (apart from the predicted mutant phenotype) or the symbiotic characteristics of the strain was targeted. A transposon-induced mutant defective in the pathway was isolated and its growth and symbiotic properties compared to the wild-type strain. No differences were observed and so the site of the transposon insertion was used to develop an integration site.

The pathway chosen was the pathway which the bacterium employs for the utilization of myo-inositol as a carbon source. The first step in the pathway is catalyzed by an NAD-dependent dehydrogenase which is inducible only by myoinositol and not by other polyols. This substrate specificity is likely to be due to the cyclical structure of myo-inositol, compared to the linear structure of other polyols. Because the pathway is not induced by other polyols, and because inositol is not naturally present in soils nor a significant component of nodule metabolites, this pathway should be silent under normal growth conditions and during symbiosis.

The originally selected mutant, designated RMB7000, was generated by random Tn5 insertional mutagenesis of *R. meliloti* strain Rm1021 (Rm1021 is a spontaneous $Sm^r$ mutant of RCR2011, described above), followed by selection for mutants unable to utilize the sugar inositol as sole carbon source. It is not known if the mutated locus, designated ino, is a structural or a regulatory gene. However, no detectable inositol dehydrogenase enzyme activity was found when the mutant strain RMB7000 was compared with *R. meliloti* 1021, its wild-type parent. However, RMB7000 grew similarly to strain Rm1021 on defined media containing glucose as carbon source, and on complex media. In plant biomass assays no detectable differences were observed between the mutant strain and *R. meliloti* 1021 parent. Furthermore, strains RMB7000 and Rm1021 formed approximately equal numbers of nodules when used as a mixed inoculum, indicating that the ino mutation did not affect the competitive ability of the strain. On this basis, the ino region was selected as an appropriate site for integration of desired constructs into the Rhizobium genome.

The ino region has been mapped to pRmSU47b, one of the two major megaplasmids of *R. meliloti*. It should be noted that both megaplasmids are extremely large (greater than 500 kb) and are not self-transmissible to other bacteria at a detectable frequency. These plasmids are, in essence, "mini-chromosomes" and are considered stable and essential parts of the *R. meliloti* genome.

Figure 22:
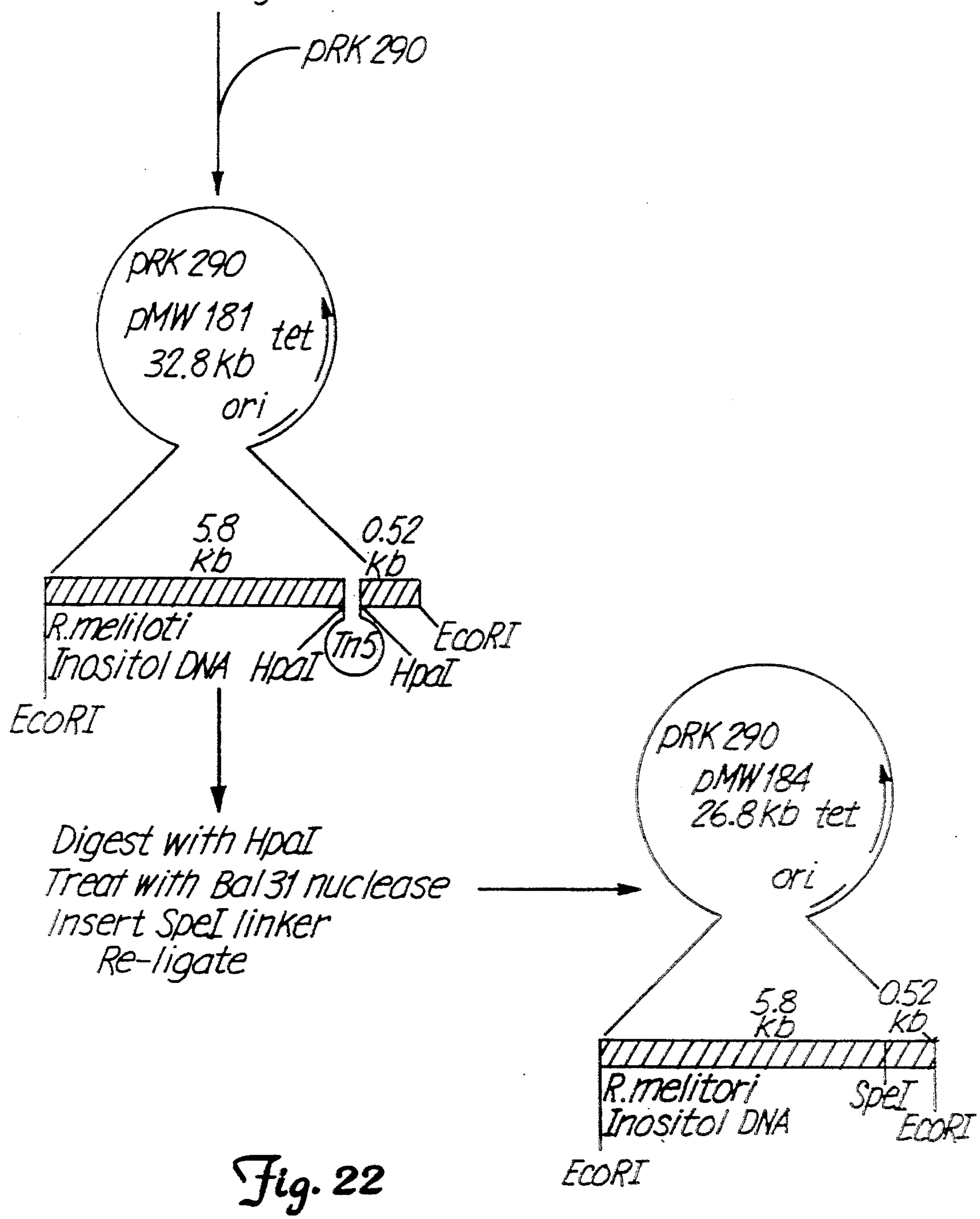
FIG. 22 is a diagram of the construction of pMW184.

To create an integration vector, the Tn5 insert of the original mutant *R. meliloti* RMB7000 was isolated on a 12 kb EcoRI fragment and cloned into pRK290 (Ditta et al., (1980) supra), creating plasmid pMW181 (FIG. 22). Plasmid pMW181 was digested with HpaI to excise the bulk of the Tn5 sequence, digested with Ba131 to remove the remaining Tn5 sequences, and re-ligated with an SpeI linker, creating plasmid pMW184 (FIG. 22). The EcoRI fragment in pMW184 was found to be about 300 bp smaller than the corresponding wild-type fragment, indicating that the Ba131 treatment resulted in deletion of ino DNA as well as Tn5 DNA. Nucleotide sequence analysis in both directions from the unique SpeI site in pMW184 confirmed that no Tn5 sequences remained. The unique SpeI site can be used to insert DNA fragments with SpeI or XbaI ends. DNA inserted into the SpeI site of pMW184 can then be inserted into the *R. meliloti* genome through homologous recombination (i.e., double crossover) of the flanking ino sequences, using standard genetic techniques.

The method of homologous recombination ensures that integration occurs at the predicted site. Furthermore, one knows that the only sequences inserted into the genome are those that are inserted into the ino region in vitro. A portion of the homologous ino region carried on the plasmid will also replace the identical genomic DNA as a result of the homologous recombination, resulting in transfer of the ino deletion of pMW184 into the genome.

Strain Construction

The cassettes were transferred to the appropriate integration vector and integrated into either the inositol or P3 integration site using the incompatibility approach described above. When the nptII gene was used as the selectable marker neomycin (50 μg/ml) was added to the media. The presence of the cassette(s) in each of the integration sites was confirmed by Southern blot analysis.

In this way the following strains were constructed in *R. meliloti* strains RCR2011 and PC that had the enhancement cassettes in the following arrangements;

1) nifA/dctA/Ω dual cassette at the P3 locus,
2) nifA/dctA/Ω dual cassette at the inositol locus,
3) nifA/nptII cassette at P3 plus the dctABD/Ω cassette at inositol, and
4) nifA/nptII cassette at inositol plus the dctABD/Ω cassette at P3.1

Such strains may exhibit increased competitiveness and increased nitrogen fixing ability compared to their parental strains.

Other Embodiments

Other embodiments are within the following claims, e.g., strains can be made more competitive by increasing dct expression by engineering high expressing promoters to the native gene or by altering the organism so as to stabilize mRNA necessary for dct gene expression.

---

What is claimed is:

1. A method for increasing occupancy of plant nodules in soil or vermiculite with modified Rhizobium or Bradyrhizobium bacteria, comprising:

making modified Rhizobium or Bradyrhizobium bacteria having, in addition to endogenous dctA, B, and D genes, an exogenous DNA sequence comprising a dctA gene under the control of an nptII promoter; adding a seed coating material to the bacteria to form a mixture; coating seeds of nodulating plants with the mixture; and planting said seeds in soil or vermiculite.

2. The method of claim 1 wherein the exogenous sequence further comprises a dctB gene.

3. The method of claim 1 wherein the exogenous DNA sequence further comprises a dctD gene.

4. The method of claim 1 wherein said bacteria further include an exogenous nifA gene.

5. The method of claim 4 wherein said bacteria are capable of nodulating a legume.

6. The method of claim 5, wherein said bacteria are capable of nodulating a soybean plant.

7. The method of claim 6, wherein said bacteria are *Bradyrhizobium japonicum*.

8. The method of claim 5, wherein said bacteria are capable of nodulating an alfalfa plant.

9. The method of claim 8, wherein said bacteria are *Rhizobium meliloti*.

10. The method of claim 1, wherein the exogenous DNA sequence increases the dicarboxylic acid membrane permease activity of the modified bacteria as compared to unmodified bacteria, and wherein the increase in dicarboxylic acid membrane permease activity increases the competitiveness of the modified bacteria compared to unmodified bacteria.

11. The method of claim 1, wherein the exogenous DNA sequence increases the dicarboxylic acid membrane permease activity of the modified bacteria as compared to unmodified bacteria, and wherein the increase in dicarboxylic acid membrane permease activity increases the nitrogen fixing capacity of said modified bacteria.

12. A method for increasing occupancy of plant nodules in soil or vermiculite with modified Rhizobium or Bradyrhizobium bacteria, comprising:

making modified Rhizobium or Bradyrhizobium bacteria having at least two DNA sequences encoding a dctA gene product, wherein expression of one of the DNA sequences is controlled by a constitutive promoter; adding a seed coating material to the bacteria to form a mixture; coating seeds of nodulating plants with the mixture; and planting said seeds in soil or vermiculite.

13. A composition for increasing occupancy of plant nodules in soil or vermiculite with modified Rhizobium or Bradyrhizobium bacteria, comprising an agriculturally acceptable carrier in combination with either Rhizobium or Bradyrhizobium bacteria which have been modified to have, in addition to endogenous dctA, B, and D genes, an exogenous DNA sequence comprising a dctA gene under the control of an nptII promoter.

14. The composition of claim 13, wherein said bacteria further include an exogenous nifA gene.

* * * * *